(12) United States Patent
Marks et al.

(10) Patent No.: US 7,750,175 B2
(45) Date of Patent: Jul. 6, 2010

(54) ORGANIC LIGHT-EMITTING DIODES AND RELATED HOLE TRANSPORT COMPOUNDS

(75) Inventors: Tobin J. Marks, Evanston, IL (US); Qinglan Huang, Libertyville, IL (US)

(73) Assignee: Northwestern University, Evanston, IL (US)

( * ) Notice: Subject to any disclaimer, the term of this patent is extended or adjusted under 35 U.S.C. 154(b) by 559 days.

(21) Appl. No.: 10/924,730

(22) Filed: Aug. 24, 2004

(65) Prior Publication Data

US 2005/0234256 A1    Oct. 20, 2005

Related U.S. Application Data

(63) Continuation-in-part of application No. 10/099,131, filed on Mar. 15, 2002, now Pat. No. 6,939,625, which is a continuation-in-part of application No. 09/187,891, filed on Nov. 6, 1998, now Pat. No. 6,399,221, which is a continuation-in-part of application No. 08/673,600, filed on Jun. 25, 1996, now Pat. No. 5,834,100.

(51) Int. Cl.
*C07F 7/10* (2006.01)
*H01L 51/54* (2006.01)

(52) U.S. Cl. .................. 556/424; 556/413; 556/465; 556/489; 564/434

(58) Field of Classification Search ................. 556/413, 556/424
See application file for complete search history.

(56) References Cited

U.S. PATENT DOCUMENTS

| | | | | |
|---|---|---|---|---|
| 5,101,055 | A * | 3/1992 | Dinh et al. ................... | 556/413 |
| 5,187,310 | A * | 2/1993 | Mishima et al. .............. | 556/413 |
| 5,830,972 | A * | 11/1998 | Ueda et al. ..................... | 528/38 |
| 5,834,100 | A * | 11/1998 | Marks et al. ................. | 428/209 |
| 6,046,348 | A * | 4/2000 | Yamada et al. .............. | 556/413 |
| 6,215,011 | B1 * | 4/2001 | Bishop ....................... | 556/413 |
| 6,369,258 | B1 * | 4/2002 | Ueda et al. ................... | 556/487 |
| 6,399,221 | B1 * | 6/2002 | Marks et al. ................. | 428/690 |
| 6,939,625 | B2 * | 9/2005 | Marks et al. ................. | 428/690 |
| 2004/0086794 | A1 * | 5/2004 | Yamada et al. ................ | 430/56 |

OTHER PUBLICATIONS

Grant & Hackh's Chemical Dictionary, 5th ed., McGraw-Hill, Inc. (1987), p. 24.*

* cited by examiner

*Primary Examiner*—Marie R. Yamnitzky
(74) *Attorney, Agent, or Firm*—Reinhart Boerner Van Deuren s.c.

(57) ABSTRACT

New organic light-emitting diodes and related hole transport compounds and methods for fabrication, using siloxane self-assembly techniques.

8 Claims, 21 Drawing Sheets

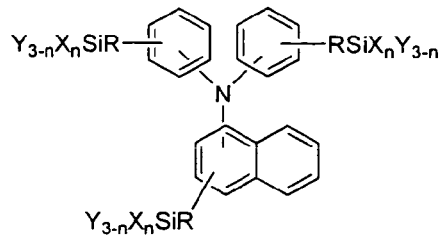
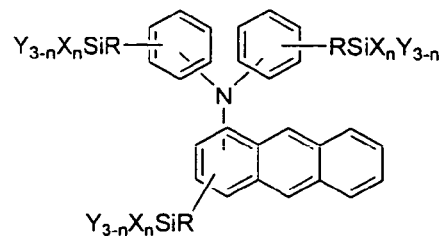
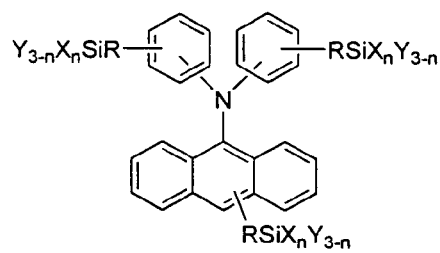
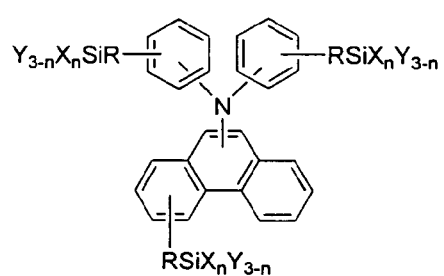
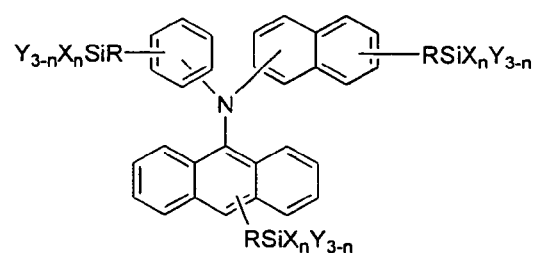
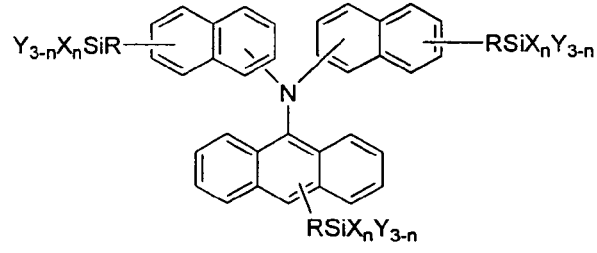
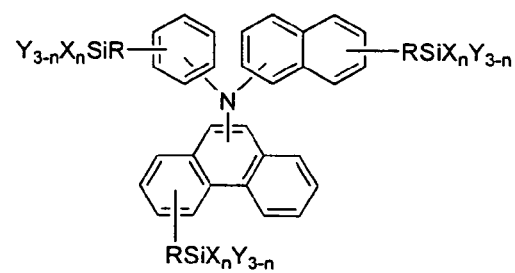
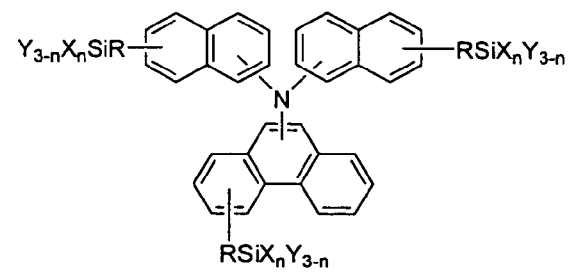
FIG. 2F

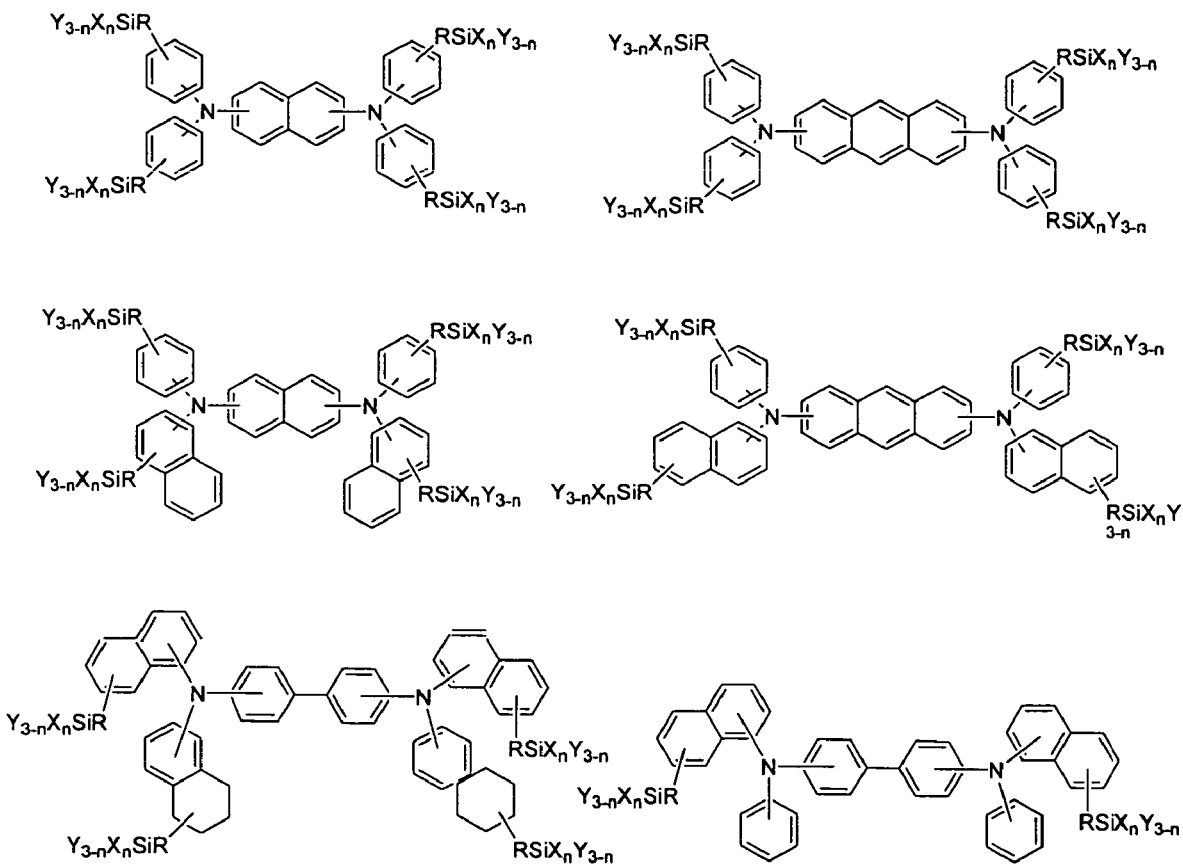
FIG. 2F con't

Route 1
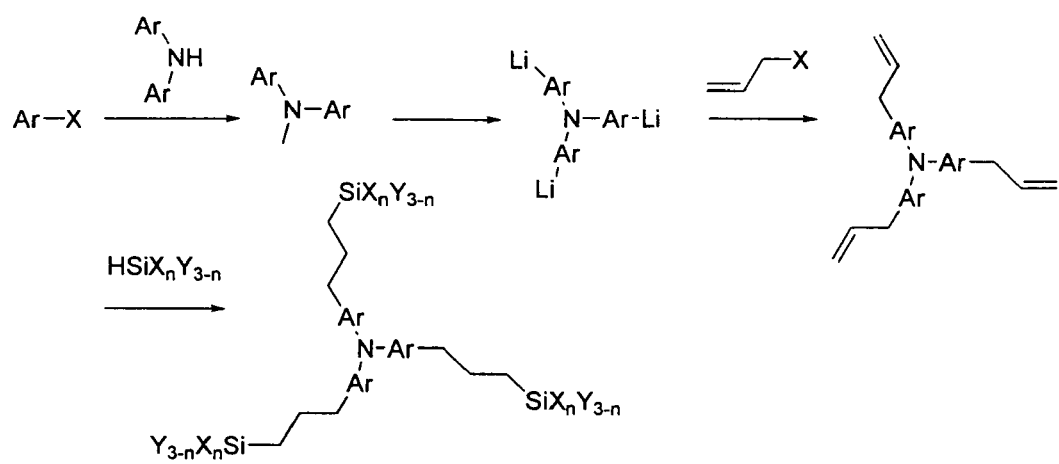
Route 2
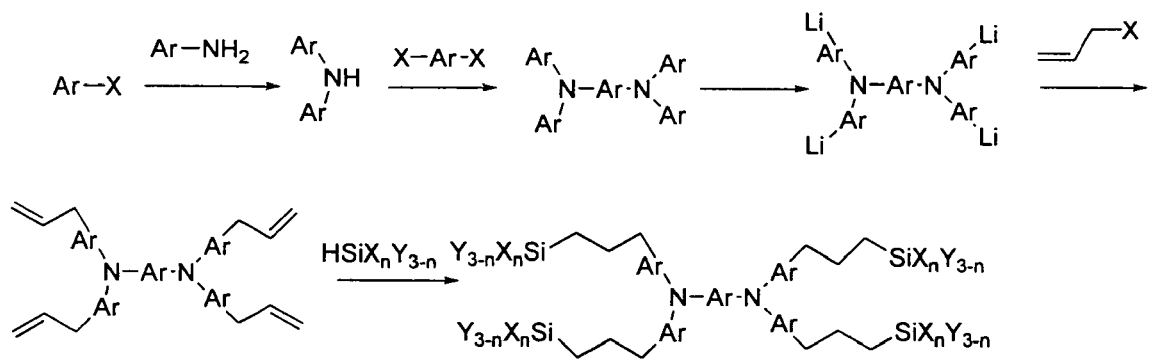
FIG. 2G (1) ITO
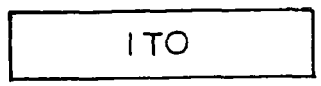
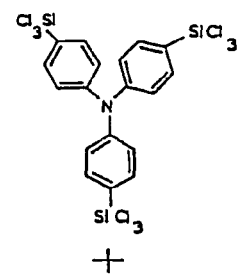
+
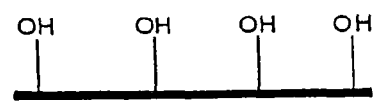
(2) ITO + HTL
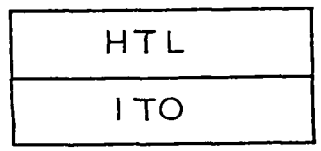
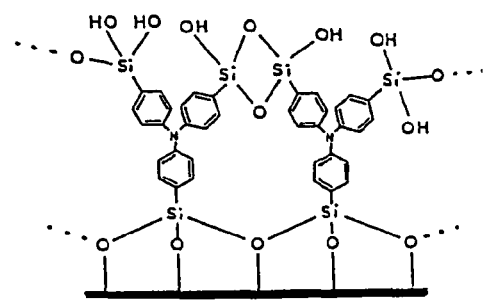
(3) ITO + HTL + ETL
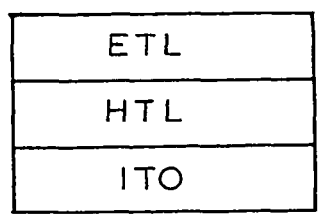
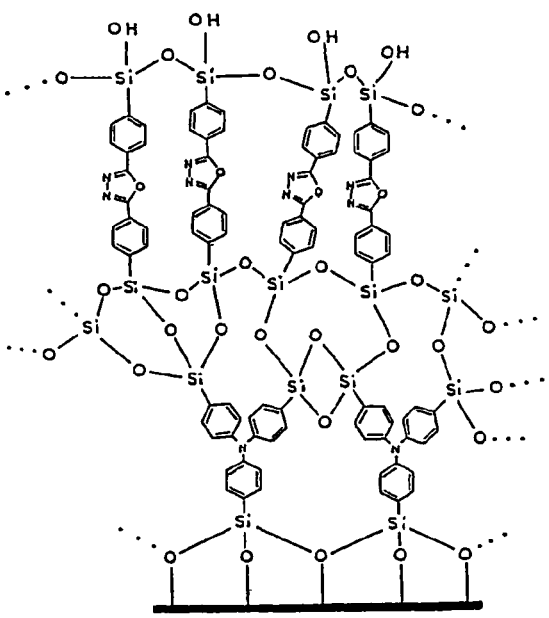
F I G. 5A Block Representation
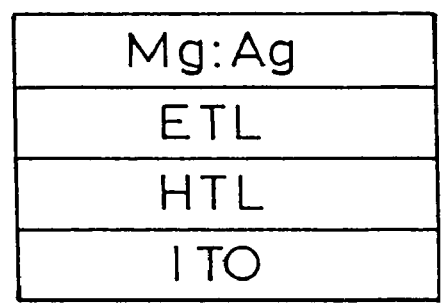
Molecular Representation
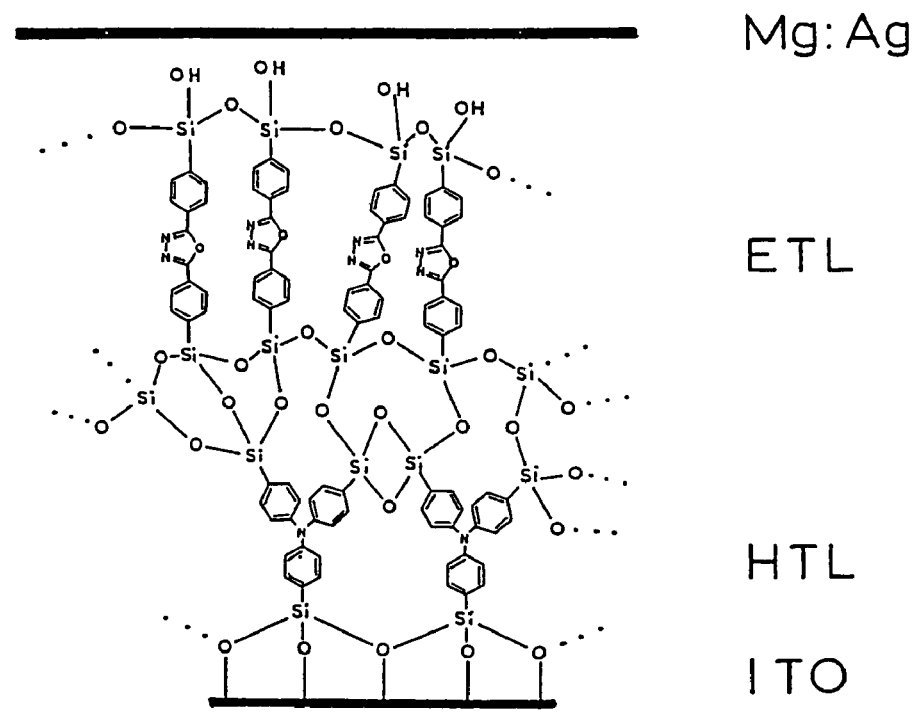
FIG. 5B

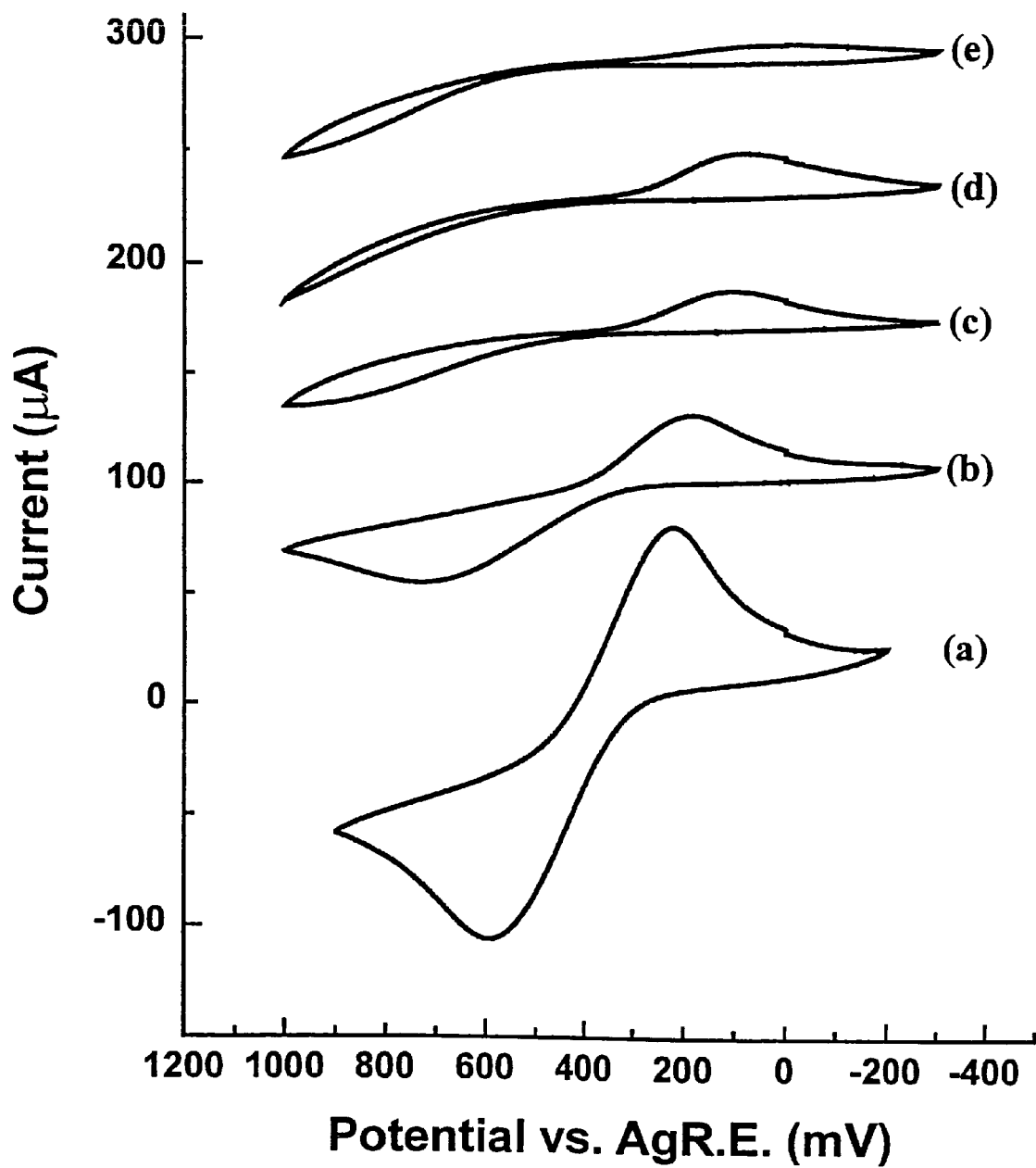

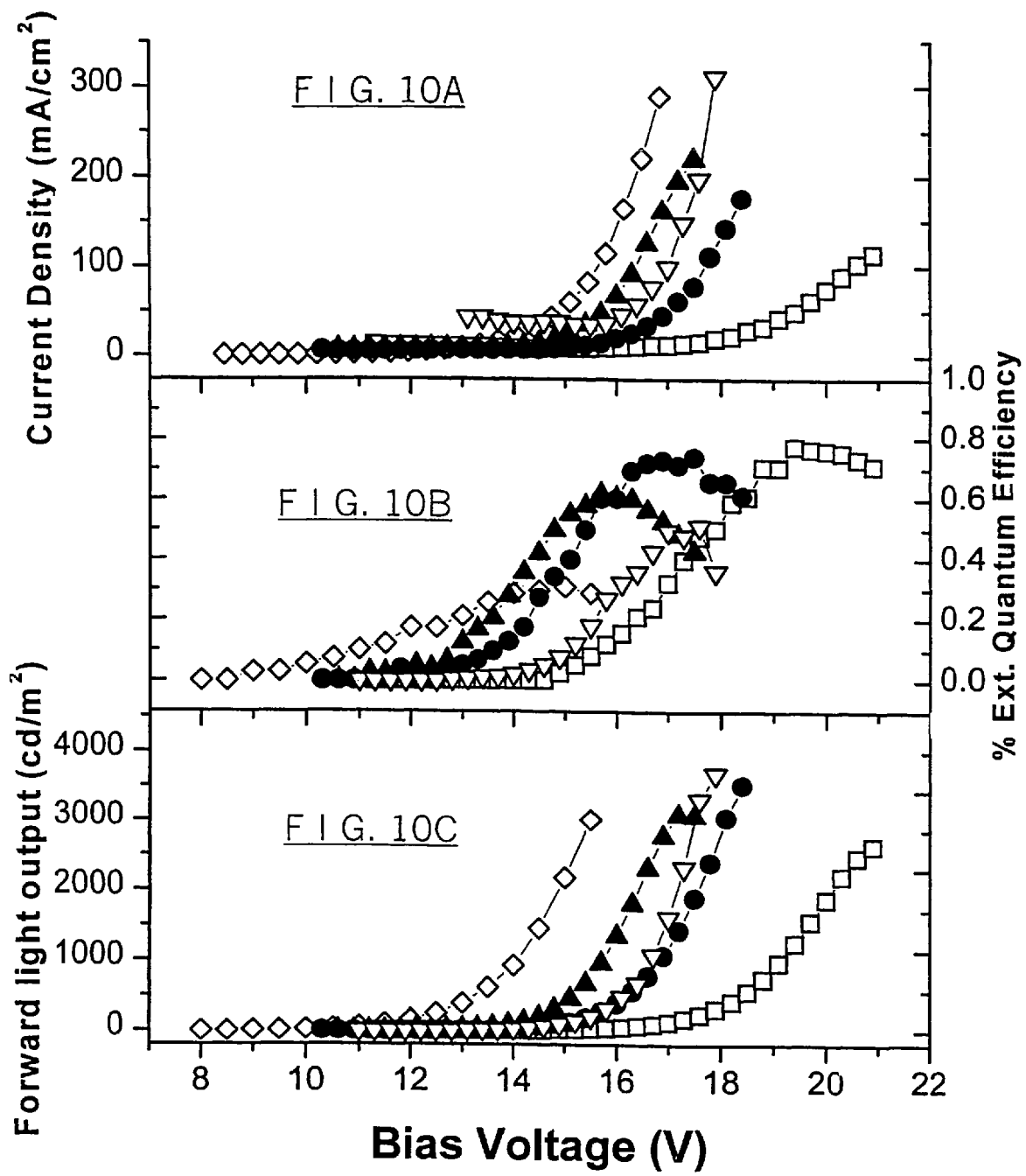

ORGANIC LIGHT-EMITTING DIODES AND RELATED HOLE TRANSPORT COMPOUNDS

This application is a continuation-in-part of and claims priority benefit from application Ser. No. 10/099,131 filed on Mar. 15, 2002, and issued as U.S. Pat. No. 6,939,625, which is a continuation-in-part of application Ser. No. 09/187,891, filed on Nov. 6, 1998 and issued as U.S. Pat. No. 6,399,221, which is a continuation-in-part of application Ser. No. 08/673,600, filed on Jun. 25, 1996, and issued as U.S. Pat. No. 5,834,100, each of which are incorporated herein by reference in their entirety.

The United States Government has certain rights to this invention pursuant to Grant Nos. N0014-95-1-1319 and DMR-00769097 from the Office of Naval Research and National Science Foundation, respectively, to Northwestern University.

BACKGROUND OF THE INVENTION

This invention relates generally to organic electroluminescent devices with organic films between anodic and cathodic electrodes, and more particularly to such devices and methods for their assembly using the condensation of various silicon moieties.

Organic electroluminescent devices have been known, in various degrees of sophistication, since the early 1970's. Throughout their development and consistent with their function and mode of operation, they can be described generally by way of their physical construction. Such devices are characterized generally by two electrodes which are separated by a series of layered organic films that emit light when an electric potential is applied across the two electrodes. A typical device can consist, in sequence, of an anode, an organic hole injection layer, an organic hole transport layer, an organic electron transport layer, and a cathode. Holes are generated at a transparent electrode, such as one constructed of indium-tin-oxide, and transported through a hole-injecting or hole-transporting layer to an interface with an electron-transporting or electron-injecting layer which transports electrons from a metal electrode. An emissive layer can also be incorporated at the interface between the hole-transporting layer and the electron-transporting layer to improve emission efficiency and to modify the color of the emitted light.

Significant progress has been made in the design and construction of polymer- and molecule-based electroluminescent devices, for light-emitting diodes, displays and the like. Other structures have been explored and include the designated "DH" structure which does not include the hole injection layer, the "SH-A" structure which does not include the hole injection layer or the electron transport layer, and the "SH-B" structure which does not include the hole injection layer or the hole transport layer. See, U.S. Pat. No. 5,457,357 and in particular col. 1 thereof, which is incorporated herein by reference in its entirety.

The search for an efficient, effective electroluminescent device and/or method for its production has been an ongoing concern. Several approaches have been used with certain success. However, the prior art has associated with it a number of significant problems and deficiencies. Most are related to the devices and the methods by which they are constructed, and result from the polymeric and/or molecular components and assembly techniques used therewith.

The fabrication of polymer-based electroluminescent devices employs spin coating techniques to apply the layers used for the device. This approach is limited by the inherently poor control of the layer thickness in polymer spin coating, diffusion between the layers, pinholes in the layers, and inability to produce thin layers which leads to poor light collection efficiency and the necessity of high D.C. driving voltages. The types of useful polymers, typically poly(phenylenevinylenes), are greatly limited and most are environmentally unstable over prolonged use periods.

The molecule-based approach uses vapor deposition techniques to put down thin films of volatile molecules. It offers the potential of a wide choice of possible building blocks, for tailoring emissive and other characteristics, and reasonably precise layer thickness control. Impressive advances have recently been achieved in molecular building blocks—especially in electron transporters and emitters, layer structure design (three versus two layers), and light collection/transmission structures (microcavities).

Nevertheless, further advances must be made before these devices are optimum. Component layers which are thinner than achievable by organic vapor deposition techniques would allow lower DC driving voltages and better light transmission collection characteristics. Many of the desirable component molecules are nonvolatile or poorly volatile, with the latter requiring expensive, high vacuum or MBE growth equipment. Such line-of-site growth techniques also have limitation in terms of conformal coverage. Furthermore, many of the desirable molecular components do not form smooth, pinhole-free, transparent films under these conditions nor do they form epitaxial/quasiepitaxial multilayers having abrupt interfaces. Finally, the mechanical stability of molecule-based films can be problematic, especially for large-area applications or on flexible backings.

BRIEF DESCRIPTION OF THE DRAWINGS

In FIG. 1, M is Cu, Zn, $SiCl_2$, or 2H; Q is N or C(X), where X is a substituted or unsubstituted alkyl or aryl group; and R is H, trichlorosilyl, trialkoxysilyl, or a moiety having 1 to 6 carbon atoms which can include trichlorosilyl or trialkoxysilyl groups, substituted on the $C_1$-$C_4$, $C_8$-$C_{11}$, $C_{15}$-$C_{18}$ and/or $C_{22}$-$C_{25}$ positions. In FIG. B, M is Cu, Zn, $SiCl_2$, or 2H; Q is N or C(X), where X is a substituted or unsubstituted alkyl or aryl group; and $T_1$/$T_2$ is H, trichlorosilyl, trialkoxysilyl, or a moiety having 1 to 6 carbon atoms which can include trichlorosilyl or trialkoxysilyl groups.

In FIG. 2A, $R_2$, $R_3$ and/or $R_4$ can be H, trihalosilyl, trialkoxysilyl, dihalosilyl, dialkoxysilyl, or a moiety having 1 to about 6 carbon atoms which can include dialkyldichlorosilyl, dialkyldialkoxysilyl, trichlorosilyl or trialkoxysilyl groups substituted anywhere on the aryl positions. In FIG. 2B, $Q_1$ and $Q_2$ can be substituted or unsubstituted tertiary aryl amines, such as those described with FIG. 2A; and G is a linking group to include but not limited to an alkyl, aryl, cylcohexyl or heteroatom group. In FIG. 2C, Ar is an arylene group; n is the number of arylene groups from 1- about 4; and $R_5$, $R_6$, $R_7$, and/or $R_8$ can be H, trihalosilyl, trialkoxysilyl, dihalosilyl, dialkoxysilyl or a moiety having 1 to about 6 carbon atoms which can include dialkyldichlorosilyl, dialkyldialkoxysilyl, trichlorosilyl or trialkoxysilyl groups substituted anywhere on the aryl positions.

FIG. 2F shows structure formulae, illustrating various arylamine compounds in accordance with FIGS. 2A, 2C-E, where R, X, Y and n are as provided in conjunction with FIGS. 2A, 2C-E.

FIG. 2G illustrates, schematically, synthetic routes 1 and 2 for preparation of compounds in accordance with FIGS. 2D and 2E, respectively. R, X, Y and n are as provided above with respect to FIGS. 2A and 2C-E. Reference is also made to the procedures illustrated in FIG. 11B and further described in Examples 2 and 27-28.

In FIG. 3A, $R_9$ and $R_{10}$ can be H, trihalosilyl, trialkoxysilyl, dihalosilyl, dialkoxysilyl, or a moiety having 1 to 6 carbon atoms which can include dialkyldichlorosilyl, dialkyldialkoxysilyl, trichlorosilyl or trialkoxysilyl groups substituted anywhere on the aryl positions. In FIG. 3B, M is Al or Ga; and $R_{11}$-$R_{14}$ can be H, trihalosilyl, trialkoxysilyl, dihalosilyl, dialkoxysilyl, or a moiety having 1 to 6 carbon atoms which can include dialkyldichlorosilyl, dialkyldialkoxysilyl, trichlorosilyl or trialkoxysilyl groups substituted anywhere on the aryl positions. In FIG. 3C, Ar is arylene; and $R_{15}$-$R_{18}$ can be H, trihalosilyl, trialkoxysilyl, dihalosilyl, dialkoxysilyl, or a moiety having 1 to 6 carbon atoms which can include dialkyldichlorosilyl, dialkyldialkoxysilyl, trichlorosilyl or trialkoxysilyl groups substituted anywhere on the aryl positions.

In FIGS. 4A-4C, X is O or S; and $R_{19}$-$R_{24}$ can be aryl groups substituted with the following substituents anywhere on the aryl ring: trihalosilyl, trialkoxysilyl, dihalosilyl, dialkoxysilyl, or a moiety having 1 to 6 carbon atoms which can contain dialkyldichlorosilyl, dialkyldialkoxysilyl, trichlorosilyl or trialkoxysilyl groups.

FIGS. 5A and 5B (ITO is indium-tin-oxide; HTL is hole transport layer and ETL is electron transport layer) show, schematically and in a step-wise manner by way of illustrating the present invention, use of the components/agents of Examples 1-5 and FIGS. 1-4 in the self-assembly and preparation of an organic light-emitting diode device. In particular, the molecular representation FIG. 5A illustrates the hydrolysis of an assembled silicon/silane component/agent to provide an Si—OH functionality reactive toward a silicon/silane moiety of another component, agent or conductive layer. The block and molecular representations of FIG. 5B illustrate a completed assembly.

FIG. 9 graphically shows cyclic voltametry measurements, using $10^{-3}$M ferrocene in acetonitrile, taken after successive layer (c-e) deposition and as compared to a bare ITO electrode (a). Even one capping layer (b), in accordance with this invention, effectively blocks the electrode surface. Complete blocking is observed after deposition of three or four layers. The sweep rate was 100 mV/sec, and the electrode area was about 0.7 $cm^2$.

FIGS. 10A-C graphically illustrate various utilities and/or performance characteristics (current density, quantum efficiency and forward light output, respectively, versus voltage) achievable through use of the present invention, as a function of the number of capping layers on an electrode surface. 0 layers, bare ITO (◇), 1 layer, 8 Å (□), 2 layers, 17 Å (•), 3 layers, 25 Å (▲) and 4 layers, 33 Å (▽). Reference is made to example 10.

SUMMARY OF THE INVENTION

Figure 1A:
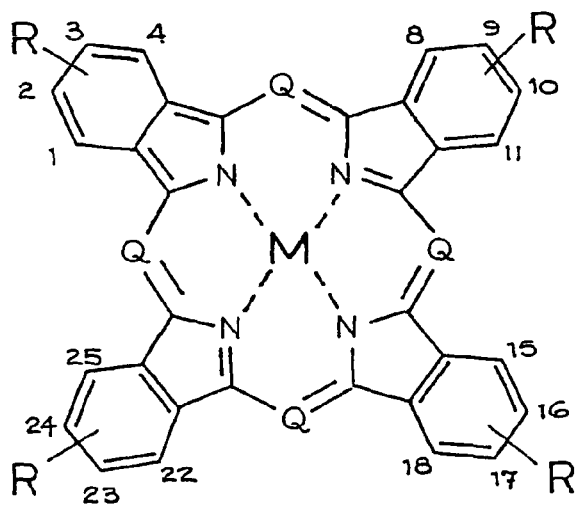
FIGS. 1A and 1B show structural formulae for porphyrinic compounds which are illustrative examples of compounds of the type which can be used as hole injection components/agents in the preparation of the molecular conductive or hole injection layers and electroluminescent media of this invention.

In light of the foregoing, it is an object of the present invention to provide electroluminescent articles and/or devices and method(s) for their production and/or assembly, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed the alternative with respect to any one aspect of this invention.

It is an object of the present invention to provide control over the thickness dimension of a luminescent medium and/or the conductive layers of such a medium, to control the wavelength of light emitted from any electroluminescent device and enhance the efficiency of such emission.

It can be another object of the present invention to provide molecular components for the construction and/or modification of an electroluminescent medium and/or the conductive layers thereof, which will allow lower driving and/or turn-on voltages than are available through use of conventional materials.

It can also be an object of the present invention to provide component molecules which can be used effectively in liquid media without resort to high vacuum or MBE growth equipment.

It can also be an object of the present invention to provide conformal conductive layers and the molecular components thereof which allows for the smooth, uniform deposition on an electrode, substrate surface and/or previously-deposited layers.

It can also be an object of this invention to provide an electroluminescent medium having a hybrid structure and where one or more of the layers is applied by a spin-coat or vapor deposition technique to one or more self-assembled conductive layers.

Other objects, features and advantages of the present invention will be apparent from this summary of the invention and its descriptions of various preferred embodiments, and will be readily apparent to those skilled in the art having knowledge of various electroluminescent devices and assembly/production techniques. Such objects, features, benefits and advantages will be apparent from the above as taken into conjunction with the accompanying examples, data, figures and all reasonable inferences to be drawn therefrom, alone or with consideration of the references incorporated herein.

This invention describes, in part, a new route to the fabrication of light-emitting organic multilayer heterojunction devices, useful for both large and small, multicolored display applications. As described more fully below, electron and hole transporting layers, as well as the emissive layer, as well as any other additional layers, are applied, developed and/or modified by molecular self-assembly techniques. As such, the invention can provide precise control over the thickness of a luminescent medium or the conductive layers which make up such a medium, as well as provide maximum light generation efficiency. Use of the present invention provides strong covalent bonds between the constituent molecular components, such that the mechanical, thermal, chemical and/or photochemical stability of such media and/or conductive layers, as can be used with an electroluminescent device, are enhanced. The use of such components also promotes conformal surface coverage to prevent cracks and pinhole deformities.

More specifically, the siloxane self-assembly techniques described herein allow for the construction of molecule-based electroluminescent media and devices. As described more fully below, various molecular components can be utilized to control the thickness dimension of the luminescent media and/or conductive layers. Nanometer dimensions can be obtained, with self-sealing, conformal coverage. The resulting covalent, hydrophobic siloxane network imparts considerable mechanical strength, as well as enhancing the resistance of such media and/or devices to dielectric breakdown, moisture intrusion, and other degradative processes.

In part, the present invention is an electroluminescent article or device which includes (1) an anode, (2) a plurality of molecular conductive layers where one of the layers is coupled to the anode with silicon-oxygen bonds and each of the layers is coupled one to another with silicon-oxygen bonds, and (3) a cathode in the electrical contact with the conductive layers. More generally and within the scope of this invention, an anode is separated from a cathode by an organic luminescent medium. The anode and the cathode are connected to an external power source by conductors. The power source can be a continuous direct, alternating or an intermittent current voltage source. A convenient conventional power source, including any desired switching circuitry, which is capable of positively biasing the anode with respect to the cathode, can be employed. Either the anode or cathode can be at ground potential.

Figure 1B:
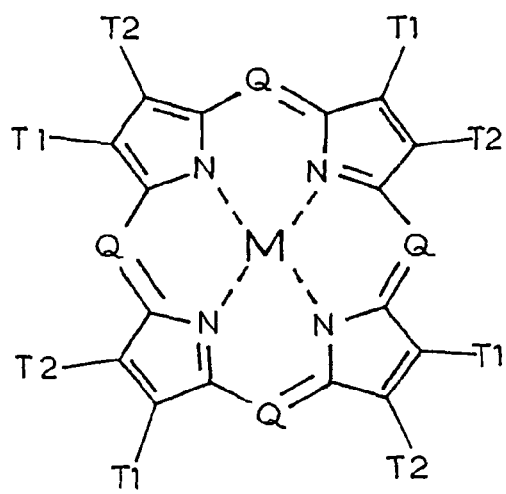

The conductive layers can include but are limited to a hole transport layer, a hole injection layer, an electron transport layer and an emissive layer. Under forward biasing conditions, the anode is at a higher potential than the cathode, and the anode injects holes (positive charge carriers) into the conductive layers and/or luminescent medium while the cathode injects electrons therein. The portion of the layers/medium adjacent to the anode forms a hole injecting and/or transporting zone while the portion of the layers/medium adjacent to the cathode forms an electron injecting and/or transporting zone. The injected holes and electrons each migrate toward the oppositely charged electrode, resulting in hole-electron interaction within the organic luminescent medium of conductive layers. A migrating electron drops from its conduction potential to a valence band in filling a hole to release energy as light. In such a manner, the organic luminescent layers/medium between the electrodes performs as a luminescent zone receiving mobile charge carriers from each electrode. Depending upon the construction of the article/device, the released light can be emitted from the luminescent conductive layers/medium through one or more of edges separating the electrodes, through the anode, through the cathode, or through any combination thereof. See, U.S. Pat. No. 5,409,783 and, in particular cols. 4-6 and FIG. 1 thereof, which is incorporated herein by reference in its entirety. As would be understood by those skilled in the art, reverse biasing of the electrodes will reverse the direction of mobile charge migration, interrupt charge injection, and terminate light emission. Consistent with the prior art, the present invention contemplates a forward biasing DC power source and reliance on external current interruption or modulation to regulate light emission.

As demonstrated and explained below, it is possible to maintain a current density compatible with efficient light emission while employing a relatively low voltage across the electrodes by limiting the total thickness of the organic luminescent medium to nanometer dimensions. At the molecular dimensions possible through use of this invention, an applied voltage of less than about 10 volts is sufficient for efficient light emission. As discussed more thoroughly herein, the thickness of the organic luminescent conductive layers/medium can be designed to control and/or determine the wavelength of emitted light, as well as reduce the applied voltage and/or increase in the field potential.

Given the nanometer dimensions of the organic luminescent layers/medium, light is usually emitted through one of the two electrodes. The electrode can be formed as a translucent or transparent coating, either on the organic layer/medium or on a separate translucent or transparent support. The layer/medium thickness is constructed to balance light transmission (or extinction) and electrical conductance (or resistance). Other considerations relating to the design, construction and/or structure of such articles or devices are as provided in the above referenced U.S. Pat. No. 5,409,783, such considerations as would be modified in accordance with the molecular conductive layers and assembly methods of the present invention.

In preferred embodiments, the conductive layers have molecular components, and each molecular component has at least two silicon moieties. In highly preferred embodiments, each silicon moiety is a halogenated or alkoxylated silane and silicon-oxygen bonds are obtainable from the condensation of the silane moieties with hydroxy functionalities. In preferred embodiments, the present invention employs an anode with a substrate having a hydroxylated surface portion. The surface portion is transparent to near-IR and visible wavelengths of light. In such highly preferred embodiments the hydroxylated surface portions include $SiO_2$, $In_2O_3 \cdot xSnO_2$, Ge and Si, among other such materials.

In conjunction with anodes and the hydroxylated surface portions thereof, the conductive layers include molecular components, and each molecular component has at least two silicon moieties. As discussed above, in such embodiments, each silicon moiety is a halogenated or alkoxylated silane, and silicon-oxygen bonds are obtainable from the condensation of the silane moieties with hydroxy functionalities which can be on a surface portion of an anode. Consistent with such preferred embodiments, a cathode is in electrical contact with the conductive layers. In highly preferred embodiments, the cathode is vapor deposited on the conductive layers, and constructed of a material including Al, Mg, Ag, Au, In, Ca and alloys thereof.

In part, the present invention is a method of producing a light-emitting diode having enhanced stability and light generation efficiency. The method includes (1) providing an anode with a hydroxylated surface; (2) coupling the surface to a hole transport layer having a plurality of molecular components, with each component having at least two silicon moieties reactive with the surface, with coupling of one of the silicon moieties to form silicon-oxygen bonds between the surface and the hole transport layer; (3) coupling the hole transport layer to an electron transport layer, the electron transport layer having a plurality of molecular components with each of the components having at least two silicon moieties reactive with the hole transport layer, with the coupling of one of the silicon moieties to form silicon-oxygen bonds between the hole and electron transport layers; and (4) contacting the electron transport layer with a cathode material.

In preferred embodiments of this method, the hole transport layer includes a hole injecting zone of molecular components and a hole transporting zone of molecular components. Likewise, in preferred embodiments, each silicon moiety is a halogenated or alkoxylated silane such that, with respect to this embodiment, coupling the hole transport layer to the electron transport layer further includes hydrolyzing the halogenated or alkoxylated silane. Likewise, with respect to a halogenated or alkoxylated silane embodiment, contacting the electron transport layer with the cathode further includes hydrolyzing the silane.

In part, the present invention is a method of controlling the wavelength of light emitted from an electroluminescent device. The inventive method includes (1) providing in sequence a hole transport layer, an emissive layer and an electron transport layer to form a medium of organic luminescent layers; and (2) modifying the thickness dimension of at least one of the layers, each of the layers including molecular components corresponding to the layer and having at least two silicon moieties reactive to a hydroxy functionality and the layers coupled one to another by Si—O bonds, the modification by reaction of the corresponding molecular components one to another to form Si—O bonds between the molecular components, and the modification in sequence of the provision of the layers.

In preferred embodiments of this inventive method, at least one silicon moiety is unreacted after reaction with a hydroxy functionality. In highly preferred embodiments, modification then includes hydrolyzing the unreacted silicon moiety of one of the molecular components to form a hydroxysilyl functionality and condensing the hydroxysilyl functionality with a silicon moiety of another molecular component to form a siloxane bond sequence between the molecular components.

In highly preferred embodiments, the silicon moieties are halogenated or alkoxylated silane moieties. Such embodiments include modifying the thickness dimension by hydrolyzing the unreacted silane moiety of one of the molecular components to form a hydroxysilyl functionality and condensing the hydroxysilyl functionality with a silane moiety of another molecular component to form a siloxane bond sequence between the molecular components.

While the organic luminescent conductive layers/medium of this invention can be described as having a single organic hole injecting or transporting layer and a single electron injecting or transporting layer, modification of each of these layers with respect to dimensional thickness or into multiple layers, as more specifically described below, can result in further refinement or enhancement of device performance by way of the light emitted therefrom. When multiple electron injecting and transporting layers are present, the layer receiving holes is the layer in which hole-electron interaction occurs, thereby forming the luminescent or emissive layer of the device.

The articles/devices of this invention can emit light through either the cathode or the anode. Where emission is through the cathode, the anode need not be light transmissive. Transparent anodes can be formed of selected metal oxides or a combination of metal oxides having a suitably high work function. Preferred metal oxides have a work function of greater than 4 electron volts (eV). Suitable anode metal oxides can be chosen from among the high (>4 eV) work function materials. A transparent anode can also be formed of a transparent metal oxide layer on a support or as a separate foil or sheet.

The devices/articles of this invention can employ a cathode constructed of any metal, including any high or low work function metal, heretofore taught to be useful for this purpose and as further elaborated in that portion of the incorporated patent referenced in the preceding paragraph. As mentioned therein, fabrication, performance, and stability advantages can be realized by forming the cathode of a combination of a low work function (<4 eV) metal and at least one other metal. Available low work function metal choices for the cathode are listed in cols. 19-20 of the aforementioned incorporated patent, by periods of the Periodic Table of Elements and categorized into 0.5 eV work function groups. All work functions provided therein are from Sze, *Physics of Semiconductor Devices*, Wiley, N.Y., 1969, p. 366.

A second metal can be included in the cathode to increase storage and operational stability. The second metal can be chosen from among any metal other than an alkali metal. The second metal can itself be a low work function metal and thus be chosen from the above-referenced list and having a work function of less than 4 eV. To the extent that the second metal exhibits a low work function it can, of course, supplement the first metal in facilitating electron injection.

Alternatively, the second metal can be chosen from any of the various metals having a work function greater than 4 eV. These metals include elements resistant to oxidation and, therefore, those more commonly fabricated as metallic elements. To the extent the second metal remains invariant in the article or device, it can contribute to the stability. Available higher work function (4 eV or greater) metal choices for the cathode are listed in lines 50-69 of col. 20 and lines 1-15 of col. 21 of the aforementioned incorporated patent, by periods of the Periodic Table of Elements and categorized into 0.5 eV work function groups.

As described more fully in U.S. Pat. No. 5,156,918 which is incorporated herein by reference in its entirety, the electrodes and/or substrates of this invention have, preferably, a surface with polar reactive groups, such as a hydroxyl (—OH) group. Materials suitable for use with or as electrodes and/or substrates for anchoring the conductive layers and luminescent media of this invention should conform to the following requirements: any solid material exposing a high energy (polar) surface to which layer-forming molecules can bind. These may include: metals, metal oxides such as $SiO_2$, $TiO_2$, MgO, and $Al_2O_3$ (sapphire), semiconductors, glasses, silica, quartz, salts, organic and inorganic polymers, organic and inorganic crystals and the like.

Inorganic oxides (in the form of crystals or thin films) are especially preferred because oxides yield satisfactory hydrophilic metal hydroxyl groups on the surface upon proper treatment. These hydroxyl groups react readily with a variety of silyl coupling reagents to introduce desired coupling functionalities that can in turn facilitate the introduction of other organic components.

The physical and chemical nature of the anode materials dictates specific cleaning procedures to improve the utility of this invention. Alkaline processes (NaOH aq.) are generally used. This process will generate a fresh hydroxylated surface layer on the substrates while the metal oxide bond on the surface is cleaved to form vicinal hydroxyl groups. High surface hydroxyl densities on the anode surface can be obtained by sonicating the substrates in an aqueous base bath.

The hydroxyl groups on the surface will anchor and orient any of the molecular components/agents described herein. As described more fully below, molecules such as organosilanes with hydrophilic functional groups can orient to form the conductive layers.

Other considerations relating to the design, material choice and construction of electrodes and/or substrates useful with this invention are as provided in the above referenced and incorporated U.S. Pat. No. 5,409,783 and in particular cols. 21-23 thereof, such considerations as would be modified by those skilled in the art in accordance with the molecular conductive layers, and assembly methods and objects of the present invention.

The conductive layers and/or organic luminescent medium of the devices/articles of this invention preferably contain at least two separate layers, at least one layer for transporting electrons injected from the cathode and at least one layer for transporting holes injected from the anode. As is more specifically taught in U.S. Pat. No. 4,720,432, incorporated herein by reference in its entirety, the latter is in turn preferably at least two layers, one in contact with the anode, providing a hole injecting zone and a layer between the hole injecting zone and the electron transport layer, providing a hole transporting zone. While several preferred embodiments of this invention are described as employing at least three separate organic layers, it will be appreciated that either the layer forming the hole injecting zone or the layer forming the hole transporting zone can be omitted and the remaining layer will perform both functions. However, enhanced initial and sustained performance levels of the articles or devices of this invention can be realized when separate hole injecting and hole transporting layers are used in combination.

Porphyrinic and phthalocyanic compounds of the type described in cols. 11-15 of the referenced/incorporated U.S. Pat. No. 5,409,783 can be used to form the hole injecting zone. In particular, the phthalocyanine structure shown in column 11 is representative, particularly where X can be, but is not limited to, an alkyltrichlorosilane, alkyltrialkoxysilane, dialkyldialkoxysilane, or dialkyldichlorosilane functionality and where the alkyl and alkoxy groups can contain 1-6 carbon atoms or is hydrogen. Preferred porphyrinic compounds are represented by the structure shown in col. 14 and where R, $T^1$ and $T^2$ can be but are not limited to an alkyltrichlorosilane, alkyltrialkoxysilane, dialkyldialkoxysilane, or dialkyldichlorosilane functionality and where the alkyl and alkoxy groups contain 1-6 carbon atoms or is hydrogen. (See, also, FIGS. 1A and 1B, herein.) Preferred phthalocyanine- and porphyrin-based hole injection agents include silicon phthalocyanine dichloride and 5,10,15,20-tetraphenyl-21H,23H-porphine silicon (IV) dichloride, respectively.

The hole transporting layer is preferably one which contains at least one tertiary aromatic amine, examples of which are as described in FIGS. 2A-2F and examples 1-2, 19-22 and 28a-28g. Such layers can comprise, without limitation, compounds of the sort provided in FIGS. 2A, 2C-F, where at least one of the aromatic moieties (i.e., phenyl in FIGS. 2A and 2C, and one of $Ar_{1-4}$ in FIGS. 2D-F) is substituted with at least one pendant silane moiety comprising a hydrolyzable silyl group (e.g., halo, alkoxy, etc.). Other exemplary arylamine core structures are illustrated in U.S. Pat. No. 3,180,730, which is incorporated herein by reference in its entirety, where the core structures are modified as described herein. Other suitable triarylamines substituted with a vinyl or vinylene radical and/or containing at least one active hydrogen containing group are disclosed in U.S. Pat. Nos. 5,409,783, 3,567,450 and 3,658,520. These patents are incorporated herein by reference in their entirety and the core structures disclosed are modified as described herein. In particular, with respect to the arylamines represented by structural formulas XXI and XXIII in cols. 15-16 of U.S. Pat. No. 5,409,703, $R^{24}$, $R^{25}$, $R^{26}$, $R^{27}$, $R^{30}$, $R^{31}$ and $R^{32}$ can be an alkyltrichlorosilane, alkyltrialkoxysilane, dialkyldialkoxysilane, or dialkyldichlorosilane functionality where the alkyl and alkoxy groups can contain 1- about 6 carbon atoms or is hydrogen.

Figure 3A:
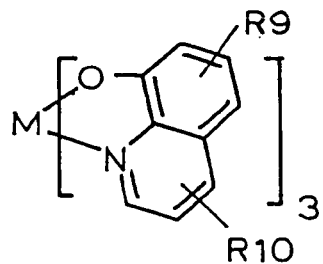
FIGS. 3A-3C show structural formulae for aryl compounds which are illustrative of examples of compounds of the type which can be used as emissive compounds/agents in the preparation of the molecular conductive layers and electroluminescent media of this invention.
Figure 3B:
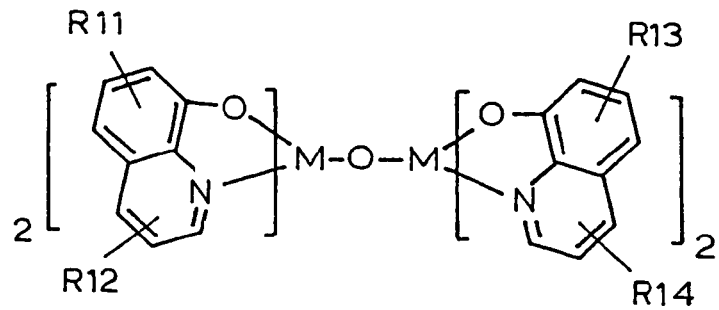
Figure 3C:
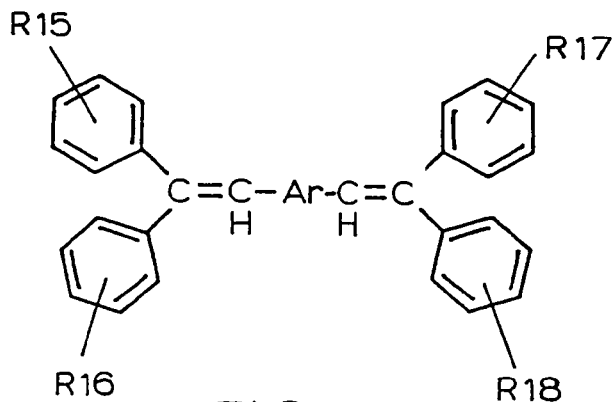

Molecular components of this invention comprising emissive agents and/or the emissive layer include those described herein in FIGS. 3A-3C and Example 5. Other such components/agents include various metal chelated oxinoid compounds, including chelates of oxine (also commonly referred to as 8-quinolinol or 8-hydroxyquinoline), such as those represented by structure III in col. 8 of the referenced and incorporated U.S. Pat. No. 5,409,783, and where $Z^2$ can be but is not limited to an alkyltrichlorosilane, alkyltrialkoxysilane, dialkyldialkoxysilane, or dialkyldichlorosilane functionality and where the alkyl and alkoxy groups can contain 1-6 carbon atoms or is hydrogen. Other such molecular components/ emissive agents include the quinolinolato compounds represented in cols. 7-8 of U.S. Pat. No. 5,151,629, also incorporated herein by reference in its entirety, where a ring substituent can be but is not limited to an alkyltrichlorosilane, alkyltrialkoxysilane, dialkyldialkoxysilane, or dialkyldichlorosilane functionality and where the alkyl and alkoxy groups can contain 1-6 carbon atoms or is hydrogen. In a similar fashion, the dimethylidene compounds of U.S. Pat. No. 5,130,603, also incorporated herein by reference in its entirety, can be used, as modified in accordance with this invention such that the aryl substituents can include an alkyltrichlorosilane, alkyltrialkoxysilane, dialkyldialkoxysilane, or dialkyldichlorosilane functionality and where the alkyl and alkoxy groups can contain 1-6 carbon atoms or is hydrogen.

Other components which can be used as emissive agents include without limitation anthracene, naphthalene, phenanthrene, pyrene, chrysene, perylene and other fused ring organic or metal-organic compounds, or as provided in col. 17 of the previously referenced and incorporated U.S. Pat. No. 5,409,783, such compounds as modified in accordance with this invention and as more fully described above. Modifiable components also include those described in U.S. Pat. Nos. 3,172,862, 3,173,050 and 3,710,167—all of which are incorporated herein by reference in their entirety.

Figure 4A:
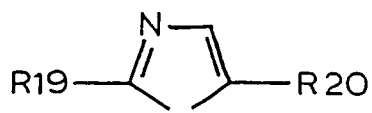
FIGS. 4A-4C show structural formulae for heterocyclic compounds which are illustrative examples of compounds of the type which can be used as electron transport components/agents in the preparation of the molecular conductive or electron transport layers and in electroluminescent media of this invention.
Figure 4B:
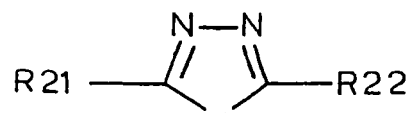
Figure 4C:
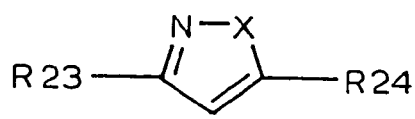

Molecular components which can be utilized as electron injecting or electron transport agents and/or in conjunction with an electron injection or electron transport layer are as described in FIGS. 4A-4C and Examples 3(a)-(d) and 4. Other such components include oxadiazole compounds such as those shown in cols. 12-13 of U.S. Pat. No. 5,276,381, also incorporated herein by reference in its entirety, as such compounds would be modified in accordance with this invention such that the phenyl substituents thereof each include an alkyltrichlorosilane, alkyltrialkoxysilane, dialkyldialkoxysilane, or dialkyldichlorosilane functionality and where the alkyl and alkoxy groups can contain 1-6 carbon atoms or is hydrogen. Likewise, such components can be derived from the thiadiazole compounds described in U.S. Pat. No. 5,336,546 which is incorporated herein by reference in its entirety.

As described above, inorganic silicon moieties can be used in conjunction with the various molecular components, agents, conductive layers and/or capping layers. In particular, silane moieties can be used with good effect to impart mechanical, thermal, chemical and/or photochemical stability to the luminescent medium and/or device. Such moieties are especially useful in conjunction with the methodology described herein. Degradation is minimized until further synthetic modification is desired. Hydrolysis of an unreacted silicon/silane moiety provides an Si—OH functionality reactive with a silicon/silane moiety of another component, agent and/or conductive layer. Hydrolysis proceeds quickly in quantitative yield, as does a subsequent condensation reaction with an unreacted silicon/silane moiety of another component to provide a siloxane bond sequence between components, agents and/or conductive layers.

In general, the molecular agents/components in FIGS. 1-4 can be prepared with a lithium or Grignard reagent using synthetic techniques known to one skilled in the art and subsequent reaction with halosilane or alkoxysilane reagents. Alternatively, unsaturated olefinic or acetylenic groups can be appended from the core structures using known synthetic techniques. Subsequently, halosilane or alkoxysilane functional groups can be introduced using hydrosilation techniques, also known to one skilled in the art. For instance, reference is made to the synthetic schemes described in Examples 2-3 and 28a-g and FIGS. 11B and 11D. Such substitution, lithiation, allylation and/or silylation techniques are as would be understood by those skilled in the art in conjunction with the schematic illustration of FIG. 2G. Purification is carried out using procedures appropriate for the specific target molecule.

It has been observed previously that the performance characteristics of electroluminescent articles of the type described herein can be enhanced by the incorporation of a layer having a modifying function between the cathode and, for instance, an electron transport or emissive layer. Previous studies show that the vapor deposition of thin layers of LiF into the various emissive and electron transport layers before deposition of the cathode improves performance in the areas of luminescence and quantum efficiency. However, this technique is limited in that the deposited LiF films are rough, degrade in air and do not form comformal, pinhole-free coatings.

The present invention is also directed to the application of self-assembly techniques to form layers which cap an electrode, provide dielectric and other functions and/or enhance performance relative to the prior art. Such capping layers are self-assembled films which are conformal in their coverage, can have dimensions less than one nanometer and can be deposited with a great deal of control over the total layer thickness. Accordingly, the present invention also includes an electroluminescent article or device which includes (1) an anode, (2) at least one molecular capping layer coupled to the anode with silicon-oxygen bonds, with each capping layer coupled one to another with silicon-oxygen bonds, (3) a plurality of molecular conductive layers, with one of the layers coupled to the capping layer with silicon-oxygen bonds and each conductive layer coupled one to another with silicon-oxygen bonds, and (4) a cathode in electric contact with a conductive layer. Likewise, and in accordance with this invention, the capping layer can be deposited on a conductive layer and/or otherwise introduced so as to be adjacent to a cathode, to enhance overall performance.

More generally and within the scope of this invention, the anode is separated from the cathode by an organic luminescent medium. The anode and cathode are connected to an external power source by conductors. The power source can be a continuous direct, alternating or intermittent current voltage source. A convenient conventional power source, including any desired switching circuitry, which is capable of positively biasing the anode with respect to the cathode, can be employed. Either the anode or cathode can be at ground potential.

In preferred embodiments, each conductive and/or capping layer has molecular components, and each molecular component has at least two silicon moieties. In highly preferred embodiments, each such conductive and/or capping component is a halogenated or alkoxylated silane, and silicon-oxygen bonds are obtainable from the condensation of the silane moieties with hydroxy functionalities. Without limitation, a preferred capping material is octachlorotrisiloxane. The anode and cathode can be chosen and/or constructed as otherwise described herein.

In part, the present invention is a method of using molecular dimension to control the forward light output of an electroluminescent device. The inventive method includes (1) providing an electrode and a molecular layer thereon, the layer coupled to the electrode with first molecular components having at least two silicon moieties reactive to a hydroxy functionality; and (2) modifying the thickness of the layer by reacting the molecular components with second components to form a siloxane bond sequence between the first and second molecular components, the second molecular components having at least two silicon moieties also reactive to a hydroxy functionality.

In preferred embodiments of this inventive method, at least one silicon moiety is unreacted after reaction with a hydroxy functionality. In highly preferred embodiments, the modification further includes hydrolyzing an unreacted silicon moiety of one of the molecular components to form a hydroxysilyl functionality and condensing the hydroxysilyl functionality with a silicon moiety of a third molecular component to form a siloxane bond sequence between the second and third molecular components. In highly preferred embodiments, the silicon moieties are halogenated or alkoxylated silane moieties.

In part, the present invention also includes any electroluminescent article for generating light upon application of an electrical potential across two electrodes. Such an article includes an electrode having a surface portion and a molecular layer coupled and/or capped thereon. The layer includes molecular components, and each component has at least two silicon moieties. The layer is coupled to the electrode with silicon-oxygen bonds. In preferred embodiments, each silicon moiety is a halogenated silane, and silicon-oxygen bonds are obtained from a condensation reaction. Likewise, and without limitation, the electrode has a substrate with a hydroxylated surface portion transparent to near-IR and visible wavelengths of light. Such a layer can be utilized to cap the electrode and/or enhance performance as otherwise described herein. More generally, in such an article or any other described herein, the luminescent medium can be constructed using either the self-assembly techniques described herein or the materials and techniques of the prior art.

The electroluminescent devices and related methods of this invention can demonstrate various interlayer/interfacial phenomena through choice of layer/molecular components and design of the resulting electroluminescent medium. As a point of reference, a number of cathode and anode interfacial structures can enhance charge injection, hence device performance. For instance, with vapor-deposited, anode/TPD (N—N'-diphenyl-N—N'-bis(3-methylphenyl)-(1-1'-biphenyl)-4-4'-diamine)/Alq (tris(quinoxalinato)Al(III))/cathode devices of the prior art, a dramatic increase in light output and quantum efficiency occurs when Å-scale LiF or CsF layers are interposed between the cathode and electron transport layer (ETL). Such thin dielectric layers are thought to lower the Al work function, thus reducing the effective electron injection barrier (energy level offset between the Alq LUMO and the Al Fermi level).

In contrast, modification of the ITO anode—hole transport layer (HTL) interface is somewhat more controllable, although similar mechanistic uncertainties pertain. Thus, a variety of ITO functionalization approaches produce phenomenologically similar effects, although less dramatic than those observed for the interposition of alkali fluoride at Al cathodes. These approaches include deposition onto ITO of nanoscale layers of various organic acids, copper phthalocyanine, or thicker (30-100 nm) layers of polyaniline or polythiophene (PEDOT), all resulting in somewhat enhanced luminous performance. Explanations for these phenomena are diverse, ranging from altering interfacial electric fields, balancing electron/hole injection fluence, confining electrons in the emissive layer, reducing injected charge back-scattering, and moderating anode Fermi level-HTL HOMO energetic discontinuities. This diversity of proposed mechanisms accurately reflects the complexity of interactions at OLED interfaces and, in many cases, the lack of necessary microstructural information.

Figure 11A:
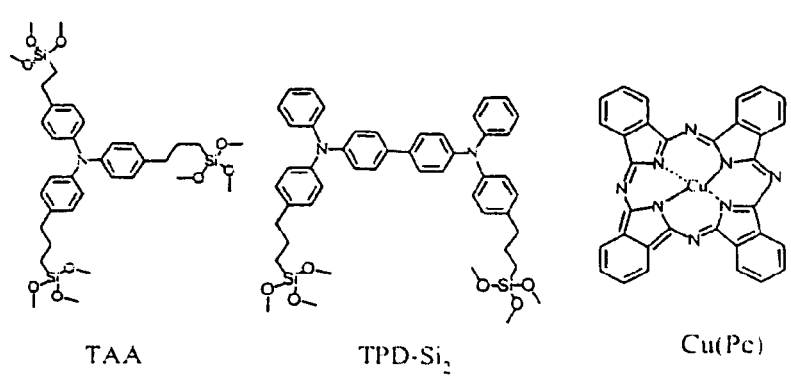
FIG. 11A shows molecular structures of hole adhesion/injection molecular components: a silyl-functionalized TAA compound (i.e., TAA-$Si_3$, shown after cross-linking), TPD-$Si_2$ (shown after crosslinking), and prior art copper phthalocyanine, Cu(Pc).

In a departure from the prior art, the present invention can be considered in the context of one or more structural relationships between an OLED anode and/or its associated organic layers. Without restriction to any one theory or mode of operation, moderation of the surface energy mismatch can be effected at a hydrophilic oxide anode-hydrophobic HTL interface, as demonstrated below using nanoscopic self-assembled silyl group functionalized amine components (see, for example, FIG. 11A and 1-4 TAA layers; 11 Å/layer). Promoting anode/ITO-HTL physical cohesion significantly enhances luminous performance and durability. Furthermore, as relates to another aspect of this invention, a silyl-group functionalized, crosslinkable amine layer having the core amine structure of the HTL component, TPD, (TPD-Si$_2$, FIG. 11A) significantly improves ITO/TPD/Alq/Al device performance and thermal durability (one metric of device stability) to an extent surprising, unexpected and unattainable with other anode functionalization structures. In contrast thereto, the commonly used copper phthalocyanine (Cu(Pc); FIG. 11A) anode functionalization layer actually templates crystallization of overlying TPD films at modest temperatures (Example 13 and FIG. 12D), consistent with the thermal instability of many Cu(Pc)-buffered OLED devices of the prior art.

Accordingly, in its broader respects, the present invention contemplates a method of using an amine molecular component to enhance hole injection across the electrode-organic interface of a light emitting diode device. The inventive method includes (1) providing an anode; and (2) incorporating an electroluminescent medium adjacent the anode, the medium including but not limited to a molecular layer, coupled to the anode, of amine molecular components substituted with at least one silyl group, and thereon a hole transport layer of molecular components having the amine structure of the aforementioned molecular layer components. The molecular layer can have at least one of an arylamine component and an arylalkylamine component, including but not limited to those monoarylamine, diarylamine and triarylamine components described in the aforementioned and incorporated U.S. Pat. No. 5,409,783, modified and/or silyl-functionalized as provided herein. Other suitable arylamine and/or arylalkylamine structures are disclosed in U.S. Pat. Nos. 3,180,730, 3,567,450 and 3,658,520, each of which is incorporated herein in its entirety, such structures as can also be modified to provide silyl-functionality in accordance herewith. Likewise, a combination of such silyl-substituted components can be employed with beneficial effect.

In preferred embodiments of this inventive method, the aforementioned amine molecular layer components are alkyl-silyl-substituted compounds of the type illustrated in FIGS. 2A and 2C-F. In highly preferred embodiments, such components include the alkylsilyl-substituted TAA and alkylsilyl substituted TPD compounds prepared as described herein. Regardless, such a molecular layer can be spin-coated on the anode surface or self-assembled, as described more fully above, to provide silicon-oxygen bonds therewith. A plurality of such molecular layers can be coupled successively on an anode surface—each layer coupled one to another with silicon-oxygen bonds—to improve structural stability and enhance device performance. As described herein and with reference to several of the following examples, hole injection can be enhanced by choice of a molecular layer with components having a structural relationship with those arylamine or arylalkylamine components of the hole transport layer. In preferred embodiments, such enhancement can be achieved through use of a silyl-functionalized TPD layer in conjunction with a TPD hole transport layer.

As such, the present invention also includes an organic electroluminescent device for generating light upon application of an electrical potential cross to electrodes. Such a device includes (1) an anode; (2) at least one molecular layer, coupled to the anode, of one or more of the aforementioned amine molecular components substituted with at least one silyl group; (3) a conductive layer of molecular components having the amine structure; and (4) a cathode in electrical contact with the anode. A preferred conductive layer includes a hole transport layer comprising components of the prior art incorporated herein by reference, or modified as described above. Preferred molecular layer components are alkylsilyl-substituted compounds of the type illustrated in FIGS. 2A and 2C-F, in particular silyl-functionalized TAA and TPD. In light of the aforementioned structural relationships and associated methodologies, a preferred conductive layer of such a device is a TPD hole transport layer, such a layer substantially without crystallization upon annealing and/or at device operation temperatures when used in conjunction with a molecular layer of components having the same or a structurally similar amine structure.

As demonstrated herein, hydrophobic amine HTL—hydrophilic anode integrity is a factor in OLED performance; poor physical cohesion contributes to inefficient hole injection and ultimately, device failure. Enhanced performance can be achieved through use of molecular layer structures which maximize interfacial cohesion and charge transport. With reference to one preferred embodiment, a conveniently applied, spincoated silyl (Si) functionalized TPD analogue, TPD-$Si_2$ (FIGS. 11A-B), structurally similar to the overlying HTL, hence well-suited to stabilizing the interface, undergoes rapid crosslinking upon spincoating from solution and subsequent thermal curing to form a dense, robust siloxane matrix with imbedded TPD hole-transport components. The thickness of these layers (~40 nm) was determined by specular X-ray reflectivity on samples deposited via identical techniques on single-crystal silicon. The RMS roughness of the TPD-$Si_2$ molecular layer films on ITO substrates of 30 Å RMS roughness is 8-12 Å by contact mode AFM. Crosslinked TPD-$Si_2$ films exhibit high thermal stability, with only 5% weight loss observed up to 400° C. by TGA, indicating substantial resistance to thermal degradation. Furthermore, cyclic voltammetry of 40 nm TPD-$Si_2$ films on ITO electrodes indicates that they support facile hole transport and are electrochemically stable.

The densely crosslinked nature of TPD-$Si_2$ molecular layer films is evident in the relatively large separation of oxidative and reductive peaks (200 mV), suggesting kinetically hindered oxidation/reduction processes with retarded counterion mobility. P. E. Smolenyak, E. J. Osburn, S.-Y. Chen, L.-K. Chau, D. F. O'Brian, N. R. Armstrong, *Langmuir* 1997, 21, 6568. That TPD-$Si_2$ film coverage on ITO is conformal and largely pinhole-free is supported by studies using a previously described ferrocene probe technique. W. Li, Q. Wang, J. Cui, H. Chou, T. J. Marks, G. E. Jabbour, S. E. Shaheen, B. Kippelen, N. Pegyhambarian, P. Dutta, A. J. Richter, J. Anderson, P. Lee, N. Armstrong, *Adv. Mater.* 1999, 11, 730. The lack of significant current flow near the formal potential for ferrocene oxidation at a TPD-$Si_2$-coated ITO working electrode indicates suppression of ferrocene oxidation, consistent with largely pinhole-free surface coverage. G. Inzelt, *Electroanalytical Chemistry*, Vol. 18, Marcel Dekker, New York, 1994, p. 89.

Such silyl-functionalized compounds are further described as having hole transport-capability in conjunction with high-performance polymeric light-emitting diodes (PLED), as described in co-pending international application no. PCT/US03/07963 filed Mar. 14, 2003, the entirety of which (in particular pages 24-25, 27-29, examples 27-32 and FIGS. 16-19) is incorporated herein by reference. As discussed therein, device structures having enhanced light emission can be fabricated without resort to a polymeric HTL. In such embodiments, as described elsewhere herein, a monolayer of any of the present silyl-functionalized arylamine compounds can be self-assembled onto an anode component. The resulting smooth, contiguous and conformal layer provides a siloxane network with embedded, electroactive arylamine hole-transporting units.

Further, as a variation of the preceding incorporated description, the present arylamine compounds can be used to fabricate a hole transport layer for PLED devices, as described in co-pending application Ser. No. 60/628,325, filed Dec. 10, 2003, the entirety of which is incorporated herein by reference. The silyl-functionalized compounds of this invention can be blended with a suitable hole-transporting/insulating polymer of the prior art. Spincoating of a blended solution, with curing, provides a cross-linked arylamine network with embedded polymeric components. Both the arylamine and polymeric components provide hole transport function and other benefits of the type described herein.

Regardless of device structure or fabrication, the arylamine compounds of this invention can be used to effect electroluminescent performance. For purposes of illustration, a series of molecules having incrementally varied structures and surface linking characteristics were prepared—as described for compounds in accordance with FIGS. 2A-G and 11A-C—and shown to form conformal, robust, self-assembled monolayers on OLED anodes. With reference to examples 27-38, it is seen that molecular structure effects on OLED charge injection, charge transport, and response characteristics can be significant.

EXAMPLES OF THE INVENTION

The following non-limiting examples and data illustrate various aspects and features relating to the articles/devices and/or methods of the present invention, including the assembly of a luminescent medium having various molecular components/agents and/or conductive layers, as are available through the synthetic methodology described herein. In comparison with the prior art, the present methods and articles/devices provide results and data which are surprising, unexpected and contrary to the prior art. While the utility of this invention is illustrated through the use of several articles/devices and molecular components/agents/layers which can be used therewith, it will be understood by those skilled in the art that comparable results are obtainable with various other articles/devices and components/agents/layers, as are commensurate with the scope of this invention.

Example 1

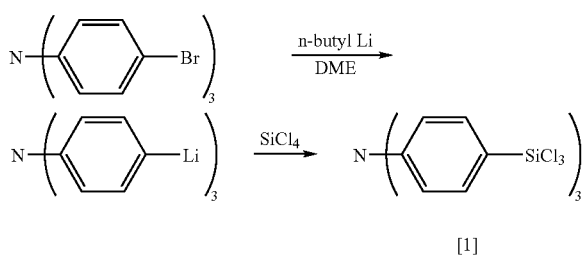

Synthesis of a Silanated Hole Transport Agent [1]. With reference to reaction scheme, above, hole transport components, agents and/or layers can be prepared, in accordance with this invention and/or for use in conjunction with light-emitting diodes and other similar electroluminescent devices. Accordingly, 500 mg. (1.0 mmole) of trisbromophenylamine (Aldrich Chemical Company) was dissolved in 30 ml of dry dimethoxyethane (DME). This solution was cooled to −45° C. and 1.2 ml (3.3 mmole) of a 2.5 M solution of n-butyl lithium in hexane was added to the reaction mixture. The entire mixture was then slowly warmed to 20° C. After stirring at 20° C. for an additional hour, the solvent was removed in vacuo. The resulting white precipitate was washed (3×20 ml) with dry pentane and redissolved in 30 ml dry DME. This solution was subsequently poured into 10 ml (87 mmole) of silicon tetrachloride at a rate of 1 ml/min. The entire reaction mixture was then refluxed for two hours. The resulting supernatent was separated from the precipitate, and the solvent again removed in vacuo yielding a green-brown residue. A white solid was obtained from this residue upon sublimation at $10^{-6}$ torr. Characterization: $^1$H NMR (600 MHz, $C_6D_6$, 20° C.): δ 7.07 (d, 6H, Ar—H); δ 7.05 (d, 6H, Ar—H); EI-MS (m/z): 645 (M+).

Example 2

Figure 2A:
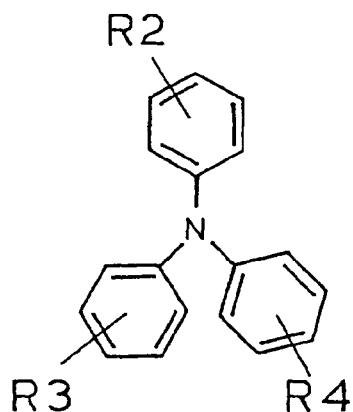
FIGS. 2A-2C show structural formulae for arylamine compounds which are illustrative examples of compounds of the type which can be used as hole transport compounds/agents in the preparation of the molecular conductive or hole transport layers and electroluminescent media of this invention.
Figure 2B:
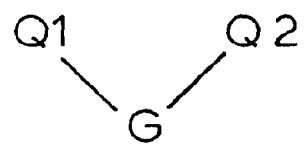
Figure 2C:
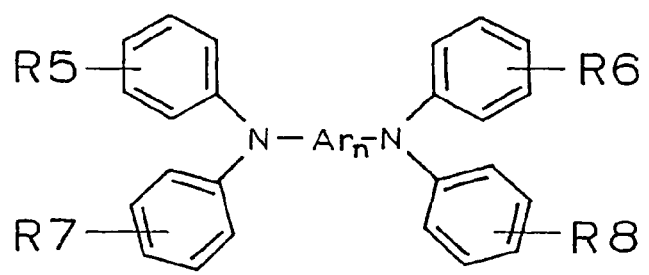
Figure 2D:
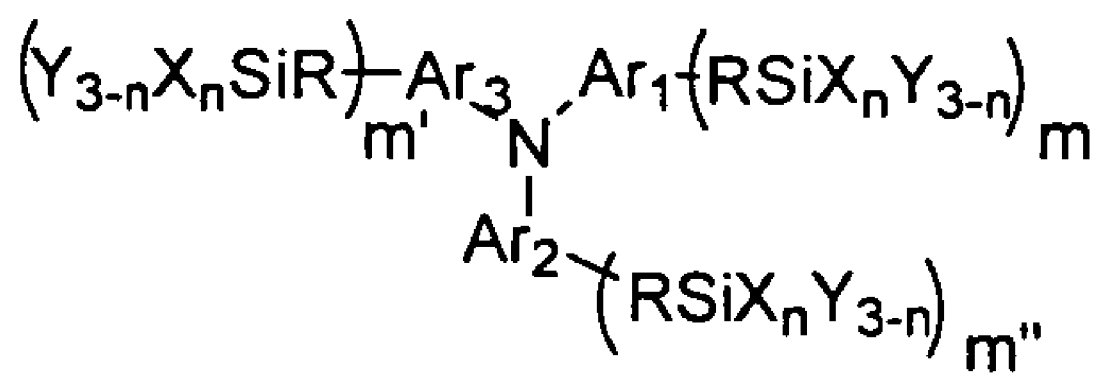
FIGS. 2D-2E show structural formulae for numerous arylamine compounds, in accordance with this invention, of the type which can also be represented by the formulae of FIGS. 2A and 2C, such compounds which can be used as or in conjunction with hole transport layers. With respect to FIGS. 2D-E, each of $Ar_{1-4}$ is independently an arylene (i.e. as understood in the art or as shown and used herein, e.g., substituted and unsubstituted phenyl, aryl, naphthyl, anthryl, phenanthryl, or other polycyclic condensed aromatic groups, heterocyclic and heteroaromatic groups) group or moiety with respect to the amino nitrogen; Ar is an arylene group or moiety (i.e., as understood in the art or as shown and used herein, e.g., a phenylene, biphenylene, naphthylene, anthrylene, phenanthrylene, or other single, multiple or polycyclic condensed aromatic and/or fused heterocyclic moiety); R is a moiety selected from alkyl, cyclic alkyl, cyclic alkylene, alkenyl, phenyl, heterocyclic, and heteroaromatic moieties; X and Y are independently selected from hydrogen, halogen, alkoxide, and amino; m, m', m" and m'" are independently integers from 0-5, providing at least one of m-m'" is from 1-5; n is independently an integer from 0-3; and o and o' are independently integers selected from 0-5, providing at least one of o and o' is 1-5. With reference to the preceding description of FIGS. 2A and 2C various combinations of R, X, Y and n can provide, without limitation, moieties associated with $R_2$-$R_8$ of FIGS. 2A and 2C having 1- about 6 carbon atoms and including dialkyldichlorosilyl, dialkyldialkoxysilyl, trichlorosilyl and/or trialkoxysilyl groups.
Figure 2E:
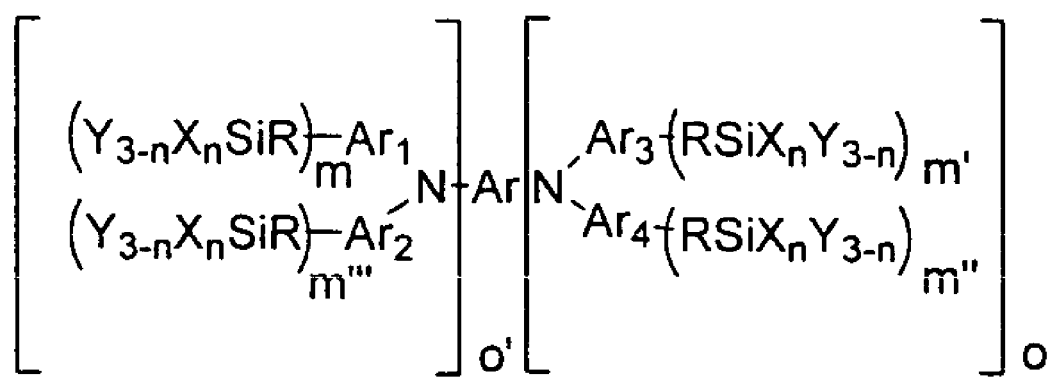

With reference to FIGS. 2A-2C and the representative arylamines provided therein, other hole transport agents and/or layers of this invention can be obtained by straightforward application of the silanation procedure described above in Example 1, with routine synthetic modification(s) and optimization of reaction conditions as would be well-known to those skilled in the art and as required by the particular arylamine. Likewise, preliminary halogenation/bromination can be effected using known synthetic procedures. Alternatively, the arylamines of FIGS. 2A-2C and other suitable substrates can be prepared using other available synthetic procedures to provide multiple silane reaction centers for use with the self-assembly methods and light-emitting diodes of this invention. Core molecular substrates of the type from which the arylamines of FIGS. 2A-2C can be prepared are described by Strukelji et al. in *Science*, 267, 1969 (1995), which is incorporated herein by reference in its entirety.

Example 3

Synthesis of a Silanated Electron Transport Agent. With reference to Examples 3(a)-(d) and corresponding reaction schemes, below, electron transport agents and/or layers can be prepared, in accordance with this invention and/or for use in conjunction with light-emitting diodes and other similar electroluminescent devices.

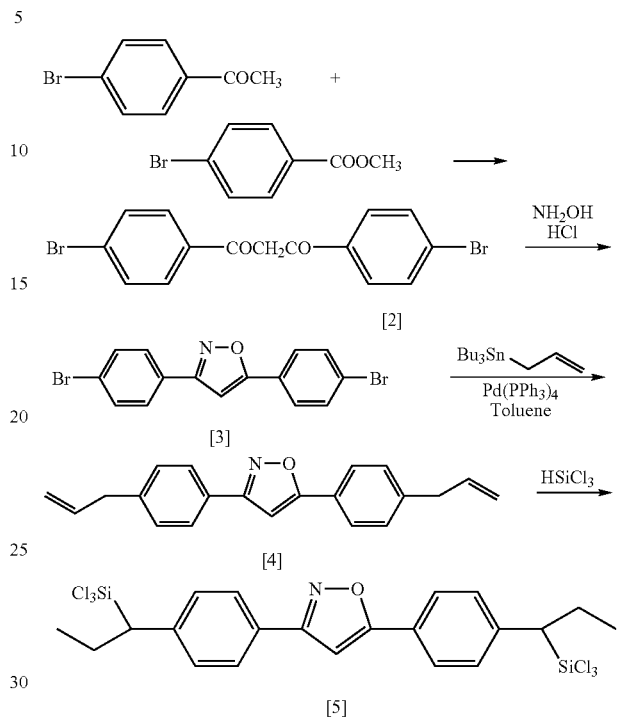

Example 3a

Synthesis of 4'-bromo-2-(4-bromobenzoyl)acetophenone [2]. In a 1-liter three neck round bottom flask, 43 g (0.2 mol) methyl 4-bromobenzoic acid and 17.6 g (0.4 mol) sodium hydride were dissolved in 200 ml dried benzene and heated to 60° C. Next, 39.8 g (0.2 mol) 4-bromoacetophenone in 100 ml dry benzene was slowly added through a dropping funnel, and 1 ml methanol was added to the flask to initiate the reaction. After the mixture was refluxed overnight, the reaction was quenched by adding methanol and pouring it into ice water. The pH of the mixture was brought down to 7.0 using 5 N sulfuric acid. A solid was collected, washed with water, and recrystallized from benzene to give a light yellow product. Characterization. Yield: 30.3 g (40%). $^1$H NMR (300 MHz, CDCl$_3$, 20° C., δ): 7.84 (d, 4H, ArH); 7.62 (d, 4H, ArH); 6.77 (s, 2H, CH$_2$). EI-MS: 382 (M+), 301, 225, 183, 157.

Example 3b

Synthesis of 3,5-bis(4-bromophenyl)isoxazole [3]. In a 250 ml round bottom flask, 4 g (10.4 mmol) of [2] was dissolved in 100 ml dry dioxane and heated to reflux, then 3.0 g (43.2 mmol) hydroxylamine hydrogen chloride in 10 ml water and 5 ml (25 mmol) 5 N NaOH was then dropped into the refluxing mixture. After 12 hours, the reaction mixture was cooled down to room temperature, and the solvent was removed in vacuo. The product was recrystallized from ethanol. Characterization. Yield: 3.41 g (85%). M.P. 218.5-219.5° C. $^1$H NMR (300 MHz, CDCl$_3$, 20° C., δ): 7.78 (d, 2H, ArH), 7.74 (d, 2H, Ar'H), 7.66 (d, 2H, ArH), 7.62 (d, 2H, Ar'H), 6.82 (s, 1H, isoxazole proton). EI-MS: 379 (M+), 224, 183, 155.

Example 3c

Synthesis of 3,5-bis(4-allylphenyl)isoxazole [4]. In a 250 ml three-neck round bottom flask, 3.77 g (10 mmol) of [3], 460 mg. (0.4 mmol) tetrakis-(triphenylphosphine)palladium, and 7.28 g (22 mmol) tributylallyltin were dissolved in 100 ml. dried toluene and degassed with nitrogen for 30 min. The mixture was heated to 100° C. for 10 h, then cooled down to room temperature. Next, 50 ml. of a saturated aqueous ammonium fluoride solution was subsequently added to the mixture. The mixture was extracted with ether, and the combined organic layer was washed by water, then brine, and finally dried over sodium sulfate. The solvent was removed in vacuo. The residue was purified by column chromatography. (first, 100% hexanes, then chloroform:hexanes [80:20]). Characterization. Yield: 1.55 g (57%). $^1$H NMR (300 MHz, CDCl$_3$, 20° C., δ): 7.78 (d, 2H, ArH), 7.74 (d, 2H, Ar'H), 7.34 (d, 2H, ArH), 7.30 (d, 2H, Ar'H), 6.78 (s, 1H, isoxazole proton), 5.96 (m, 2H, alkene H), 5.14 (d, 4H, terminal alkene H), 3.44 (d, 4H, methylene group). EI-MS: 299 (M+), 258, 217.

Example 3d

Synthesis of 3,5-bis(4-(N-trichlorosilyl)propylphenyl) isoxazole [5]. To 2 ml of THF was added 5 mg of [4], 3.4 μl of HSiCl$_3$ and 0.8 mg. of H$_2$PtCl$_6$ were added to 2 ml of THF. The reaction was heated at 50° C. for 14 h. The solvent was then removed in vacuo. A white solid was obtained from this residue upon sublimation at 10$^{-6}$ torr. Characterization. $^1$H NMR (300 MHz, d$^8$-THF, 20° C., δ): 7.72 (d, 2H, ArH), 7.68 (d, 2H, Ar'H), 7.36 (d, 2H, ArH), 7.32 (d, 2H, Ar'H), 6.30 (s, 1H, isoxazole); 2.52 (t, 2H, CH); 1.55 (m, 4H, CH$_2$); 0.85 (t, 6H, CH$_3$).

Example 4

With reference to FIGS. 4A-4C and the representative heterocycles provided-therein, other electron transport agents and/or layers of this invention can be obtained by straightforward application of the silanation procedure described above in Example 3, with routine synthetic modification(s) and optimization of reaction conditions as would be well-known to those skilled in the art and as required by the particular heterocyclic substrate. Preliminary halogenation/bromination can be effected using known synthetic procedures or through choice of starting materials enroute to a given heterocycle. Alternatively, the heterocycles of FIGS. 4A-4C and other suitable substrates can be prepared using other available synthetic procedures to provide multiple silane reaction centers for use with the self-assembly methods and light-emitting diodes of this invention. Core molecular substrates of the type from which the heterocycles of FIGS. 4A-4C can be prepared are also described by Strukelji et al. in *Science*, 267, 1969 (1995).

Example 5

With reference to FIGS. 3A-3C and the representative chromophores provided therein, emissive agents and/or layers, in accordance with this invention, can be obtained by appropriate choice of starting materials and using halogenation and silanation procedures of the type described in Examples 1-4, above. Alternatively, other chromophores can be silanated using other available synthetic procedures to provide multiple silane reaction centers for use with the self-assembly methods and light-emitting diodes of this invention. Regardless, in accordance with this invention, such emissive agents or chromophores can be used for emission of light at wavelengths heretofore unpractical or unavailable. Likewise, the present invention allows for the use of multiple agents or chromophores and construction of an emissive layer or layers such that a combination of wavelengths and/or white light can be emitted.

Example 6

Figure 6:
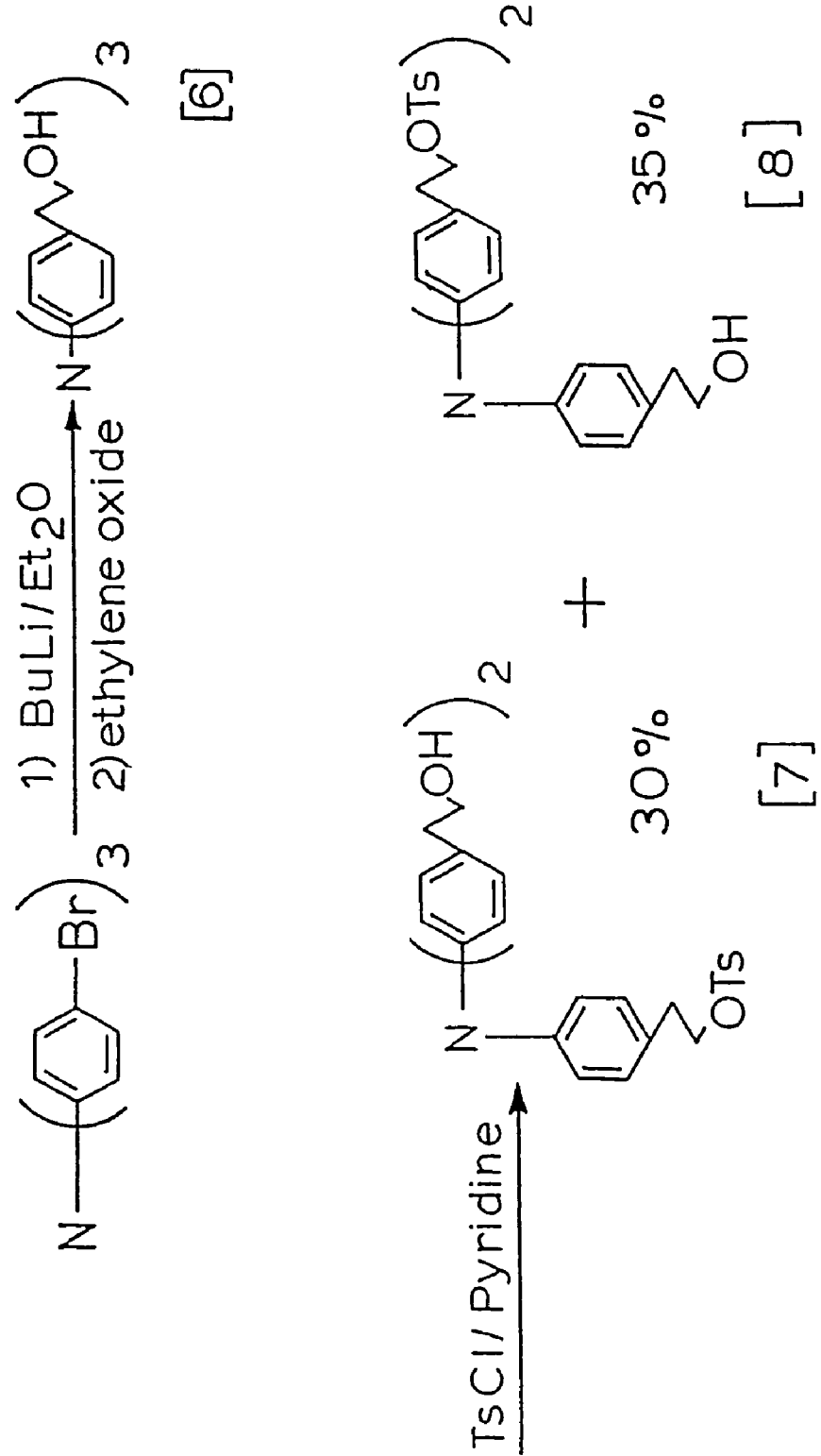
FIG. 6 shows an alternative synthetic sequence enroute to several arylamine components/agents, also in accordance with the present invention.

Examples 6(a)-6(c) together with FIG. 6 illustrate the preparation of other molecular components which can be used in accordance with this invention.

Example 6a

Synthesis of Tertiary Arylamine [6]. Together, 14.46 g (20 mmole) of tris(4-bromophenyl)amine and 500 ml of dry diethyl ether were stirred at –78° C. under a nitrogen atmosphere. Next, 112.5 ml of a 1.6 M n-butyllithium solution in hexanes was slowly added to the reaction mixture over 1.5 hours. The reaction was then warmed to –10° C. and stirred for an additional 30 minutes. The reaction was then cooled down again to –78° C. before the addition of 22 g (0.5 mole) of ethylene oxide. The mixture was stirred and slowly warmed to room temperature over 12 hours. Next, 2 ml of a dilute NH$_4$Cl solution was then added to the reaction mixture. The solvent was evaporated under vacuum yielding a light green solid. The product was purified using column chromatography. The column was first eluted with chloroform and then with MeOH:CH$_2$Cl$_2$ (5:95 v/v). The resulting light gray solid was recrystallized using chloroform to give 1.89 g. Yield: 25%. $^1$H NMR (δ, 20° C., DMSO): 2.65 (t, 6H), 3.57 (q, 6H), 4.64 (t, 3H), 6.45 (d, 6H), 7.09 (d, 6H). EI-MS: 377 (M$^+$), 346 (M$^+$–31), 315 (M$^+$–62). HRMS: 377.2002. calcd; 377.1991. Anal. Calculated for C$_{24}$H$_{27}$NO$_3$; C, 76.36; H, 7.21; N, 3.71. Found: C, 76.55; H, 7.01; N, 3.52.

Example 6b

Synthesis of Tosylated Arylamine [7]. A pyridine solution of tosyl chloride (380 mg in 5 ml) was added over 5 minutes to a pyridine solution of [6] (500 mg in 10 ml, from Example 6a) cooled to 0° C. The mixture was stirred for 12 hours, then quenched with water and extracted with chloroform. The organic extract was washed with water, 5% sodium bicarbonate, and dried with magnesium sulfate. After filtration, the chloroform solution was then evaporated to dryness under vacuum and purified using column chromatography. The column was first eluted with hexane:CHCl$_3$ (1:2 v/v) yielding [7]. $^1$H NMR (300 MHz, δ, 20° C., CDCl$_3$): 2.45 (s, 3H), 2.90 (t, 6H), 3.02 (t, 3H), 3.70 (t, 3H), 4.19 (t, 6H), 6.92 (d, 2H), 6.98 (d, 4H), 7.00 (d, 4H), 711 (d, 2H), 7.32 (d, 2H), 7.77 (d, 2H).

Example 6c

Synthesis of Tosylated Arylamine [8]. Continuing the chromatographic procedure similar for 2 (from Example 6b) but changing the eluting solvent to 100% CHCl$_3$ yielded [8]. $^1$H NMR (300 MHz, δ, 20° C., CDCl$_3$): 2.44 (s, 6H), 2.91 (t, 3H), 3.02 (t, 6H), 3.70 (t, 6H), 4.19 (t, 3H), 6.92 (d, 4H), 6.98 (d, 2H), 7.00 (d, 2H), 7.11 (d, 4H), 7.32 (d, 4H), 7.77 (d, 4H).

Example 7

Figure 7:
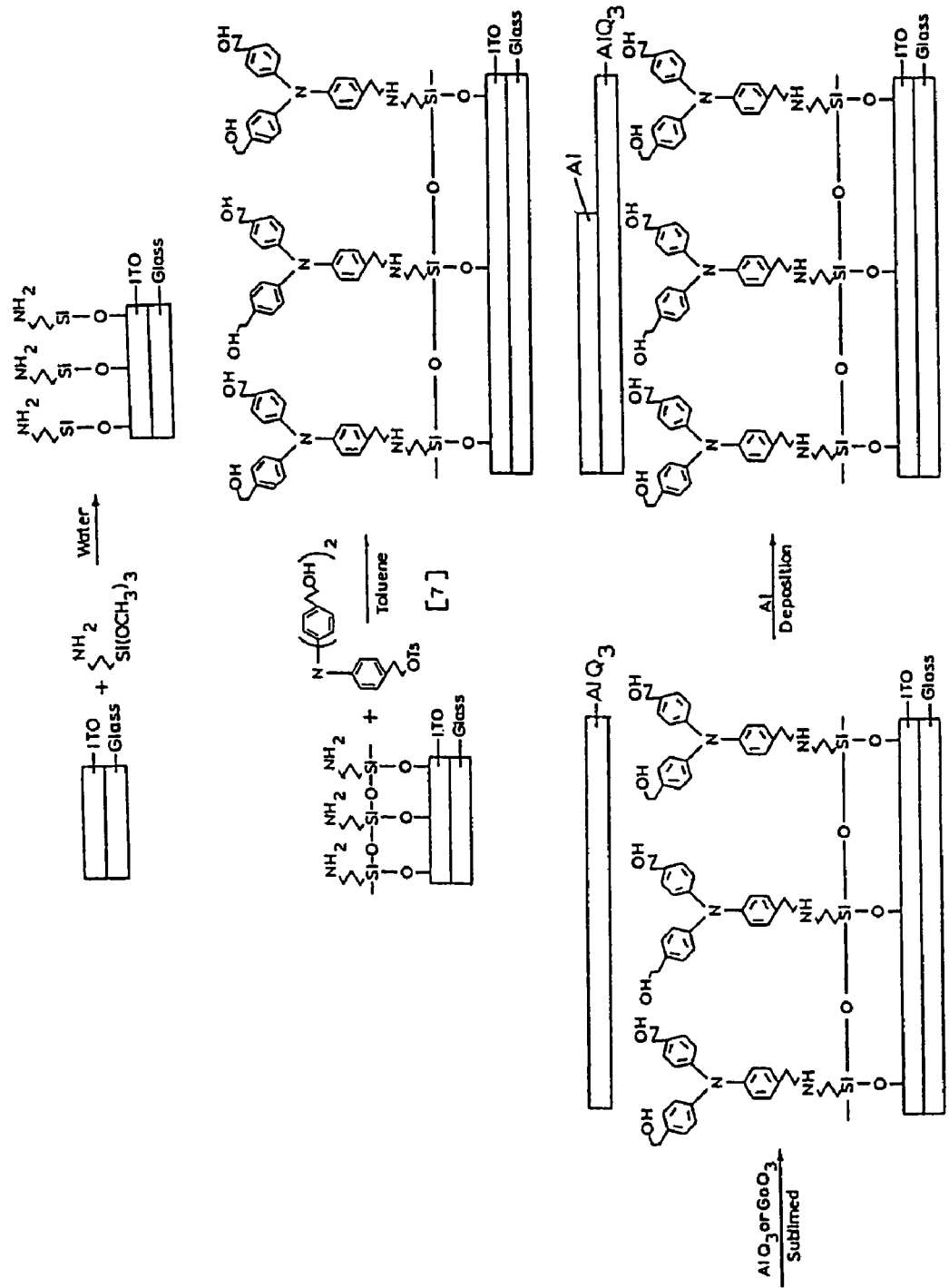
FIG. 7 shows, schematically and by way of illustrating an alternative embodiment of the present invention, use of the components/agents of FIG. 6 in the preparation of another representative electroluminescent device.

Using the arylamines of Examples 6 and with reference to FIG. 7, an electroluminescent article/device also in accordance with this invention is prepared as described, below. It is understood that the arylamine component can undergo another or a series of reactions with a silicon/silane moiety of another molecular component/agent to provide a siloxane bond sequence between components, agents and/or conductive layers. Similar electroluminescent articles/devices and conductive layers/media can be prepared utilizing the various other molecular components/agents and/or layers described above, such as in Examples 1-5 and FIGS. 1-4, in conjunction with the synthetic modifications of this invention and as required to provide the components with the appropriate reactivity and functionality necessary for the assembly method(s) described herein.

Example 7a

This example of the invention shows how slides can be prepared/cleaned prior to use as or with electrode materials. An indium-tin-oxide (ITO)-coated soda lime glass (Delta Technologies) was boiled in a 20% aqueous solution of ethanolamine for 5 minutes, rinsed with copious amounts of distilled water and dried for 1 hour at 120° C.; alternatively and with equal effect, an ITO-coated soda lime glass (Delta Technologies) was sonicated in 0.5M KOH for 20 minutes, rinsed with copious amounts of distilled water and then ethanol, and dried for 1 hour at 120° C.

Example 7b

Electroluminescent Article Fabrication and Use. The freshly cleaned ITO-coated slides were placed in a 1% aqueous solution of 3-aminopropyltrimethoxysilane and then agitated for 5 minutes. These coated slides were then rinsed with distilled water and cured for 1 hour at 120° C. The slides were subsequently placed in a 1% toluene solution of [7] (or [8] from Example 6) and stirred for 18 hours under ambient conditions. Afterwards, the slides were washed with toluene and cured for 15 minutes at 120° C. $AlQ_3$ (or $GaQ_3$; Q=quinoxalate) was vapor deposited on top of the amine-coated slides. Finally, 750-1000 Å of aluminum was vapor deposited over the metal quinolate layer. Wires were attached to the Al and ITO layers using silver conducting epoxy (CircuitWorks™), and when a potential (<7V) was applied, red, orange, and/or green light was emitted from the device.

Example 8

Figure 8:
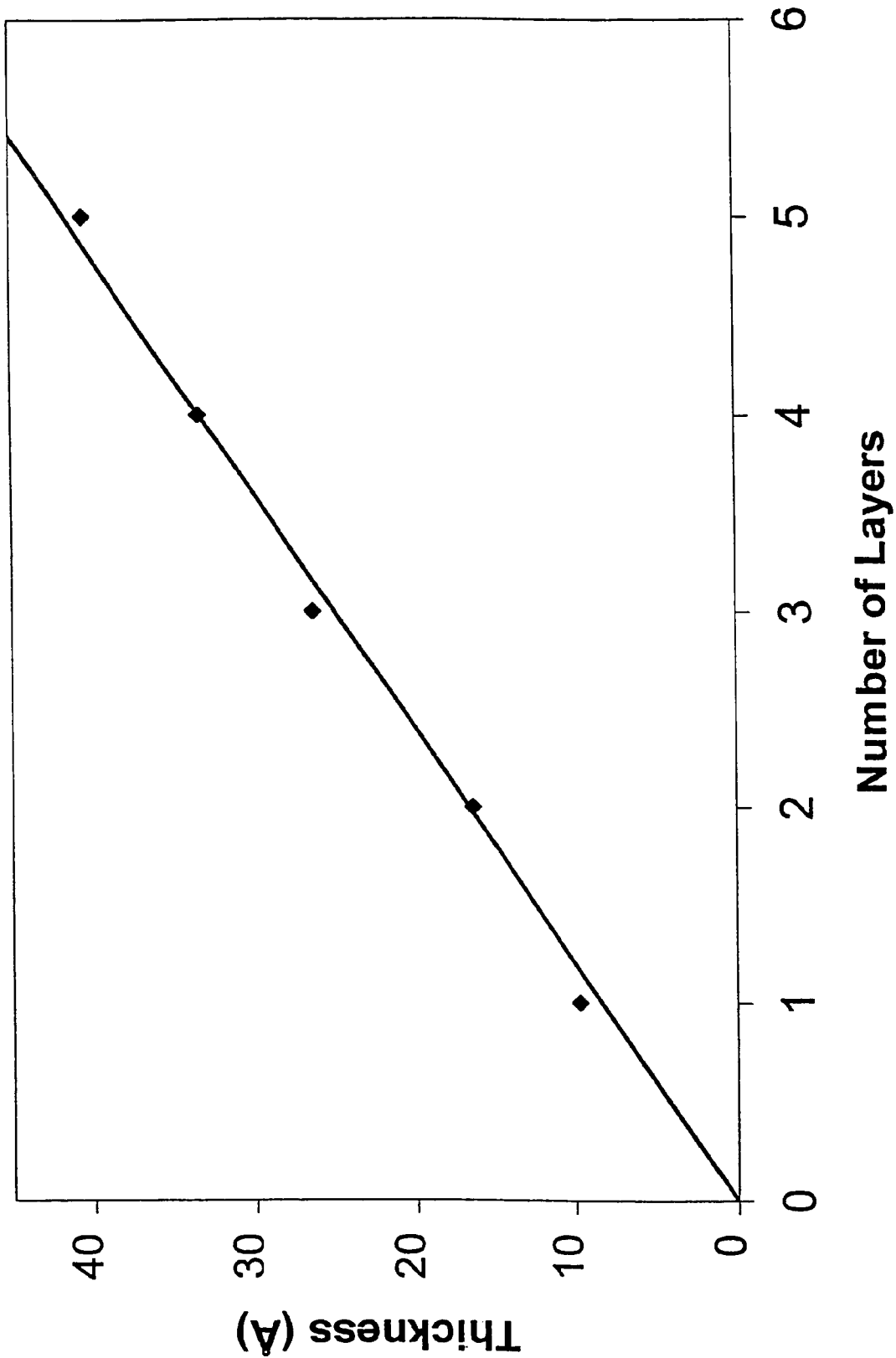
FIG. 8 graphically correlates x-ray reflectivity measurements of film thickness with the number of capping layers applied to a substrate. As calculated from the slope of the line (y=8.3184x), each layer is about 7.84 Å in dimensional thickness.

One or more capping layers comprising $Cl_3SiOSiCl_2OSiCl_3$ are successively deposited onto clean ITO-coated glass where hydrolysis of the deposited material followed by thermal curing/crosslinking in air at 125° C. yields a thin (~7.8 Å) layer of material on the ITO surface. X-ray reflectivity measurements indicate that the total film thickness increases linearly with repeated layer deposition, as seen in FIG. 8. Other molecular components can be used with similar effect. Such components include, without limitation, the bifunctional silicon compounds described in U.S. Pat. No. 5,156,918, at column 7 and elsewhere therein, incorporated by reference herein in its entirety. Other useful components, in accordance with this invention include those trifunctional compounds which cross-link upon curing. As would be well known to those skilled in the art and made aware of this invention, such components include those compounds chemically reactive with both the electrode capped and an adjacent conductive layer.

Example 9

Cyclic voltametry measurements shown in FIG. 9 using aqueous ferri/ferrocyanide show that there is considerable blocking of the electrode after the deposition of just one layer of the self-assembled capping material specified in Example 8. Other molecular components described, above, show similar utility. Almost complete blocking, as manifested by the absence of pinholes, is observed after application of three layers of capping material.

Example 10

Conventional organic electroluminescent devices consisting of TPD (600 Å)/Alq (600 Å)/Mg (2000 Å) were vapor-deposited on ITO substrates modified with the capping material specified in Example 8. FIGS. 10A-C show the behavior of these devices with varying thickness of the self-assembled capping material. These results show that such a material can be used to modify forward light output and device quantum efficiency. For a device with two capping layers, higher current densities and increased forward light output are achieved at lower voltages, suggesting an optimum thickness of capping material can be used to maximize performance of an electroluminescent article.

Example 11

This example illustrates how a capping material can be introduced to and/or used in the construction of an electroluminescent article. ITO-coated glass substrates were cleaned by sonication in acetone for 1 hour followed by sonication in methanol for 1 hour. The dried substrates were then reactively ion etched in an oxygen plasma for 30 seconds. Cleaned substrates were placed in a reaction vessel and purged with nitrogen. A suitable silane, for instance a 24 mM solution of octachlorotrisiloxane in heptane, was added to the reaction vessel in a quantity sufficient to totally immerse the substrates. (Other such compounds include those described in Example 8). Substrates were allowed to soak in the solution under nitrogen for 30 minutes. Following removal of the siloxane solution the substrates were washed and sonicated in freshly distilled pentane followed by a second pentane wash under nitrogen. Substrates were then removed from the reaction vessel washed and sonicated in acetone. Substrates were dried in air at 125° C. for 15 minutes. This process can be repeated to form a capping layer of precisely controlled thickness.

Example 12

Figure 12A:
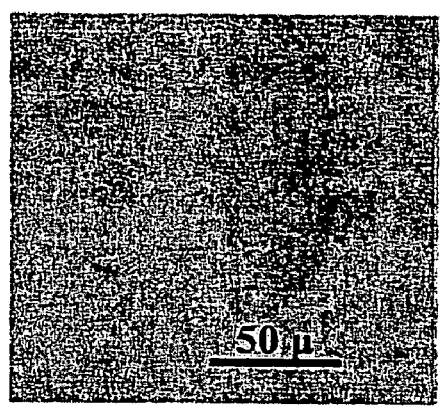
FIGS. 12A-D provide optical microscopic images of vapor-deposited TPD film (100 nm) morphology after annealing at 80° C. for 1.0 h on ITO substrates coated with a cured 40 nm thick TPD-$Si_2$ film (12A) and on bare ITO (12B); polarized optical image of TPD film (100 nm) morphology before (12C) and after (12D) annealing the bilayer structure: ITO/CuPc(10 nm)/TPD (100 nm) at 80° C. for 0.50 h.
Figure 12B:
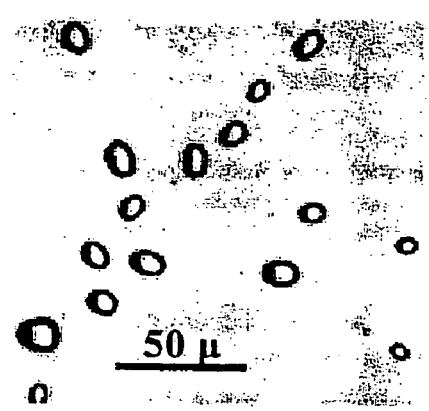

The stability of device-type $TPD-Si_2$ molecular layer/TPD hole transport layer interfaces under thermal stress (one measure of durability) was investigated by annealing ITO/TPD-$Si_2$ (40 nm)/TPD (100 nm) bilayers at 80° C. for 1.0 h. The optical image of the annealed TPD film shows no evidence of TPD de-wetting/de-cohesion (FIG. 12A), indicating that the ITO-TPD surface energy mismatch is effectively moderated by the interfacial TPD-$Si_2$ molecular layer. In contrast, the bare ITO/TPD interface exhibits catastrophic de-wetting/de-cohesion under identical thermal cycling (FIG. 12B), visible even under a layer of Alq). Despite seemingly similar cohesive effects for both TAA and TPD-Si$_2$ as interfacial buffer layers, it is reasonable to suggest that the interfacial cohesion between TPD-Si$_2$ and TPD is greater, given closer structural similarity, evidenced by comparing advancing aqueous contact angles: values for bare ITO, silyl-functionalized TAA, silyl (Si$_2$) functionalized TPD and TPD film surfaces are 0°, 45°, 70°, and 85° respectively, indicating a closer surface energy match at TPD-TPD-Si$_2$ interfaces.

Example 13

Figure 12C:
Figure 12D:
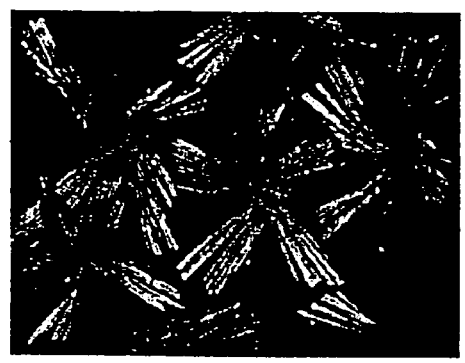

Speculation that one role of Cu(Pc) in enhancing OLED performance might be via the above adhesion mechanism led to parallel thermal studies. In contrast to a preferred alkylsilyl-substituted arylamine TPD-Si$_2$, Cu(Pc)-buffered ITO does not prevent TPD de-cohesion upon heating to temperatures near/above the TPD glass transition temperature (T$_g$). FIG. 12D illustrates the morphology of a 100 nm TPD film on 10 nm Cu(Pc) following heating at 80° C. It is clearly seen that thermal annealing induces TPD crystallization on the Cu(Pc) film surface (visible even under a layer of Alq), yielding star-shaped dendritic crystallites (as-deposited TPD films on Cu(Pc) are smooth and featureless, FIG. 12C). It is likely that such Cu(Pc)-nucleated crystallization occurs during localized heating in operating OLEDs and contributes to observed device instability.

Example 14

Figure 13A:
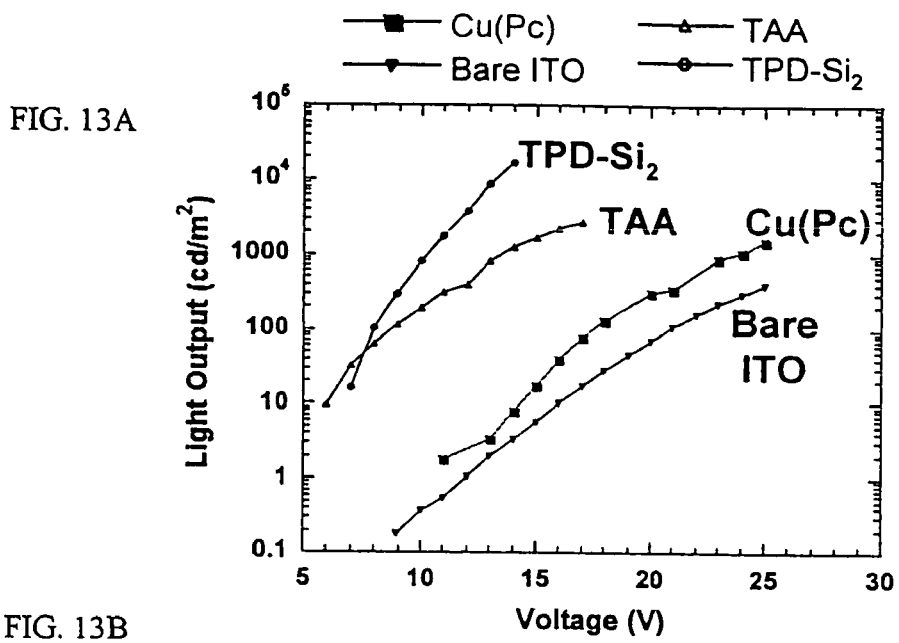
FIGS. 13A-C show, in turn, (A) light output, (B) external quantum efficiency, and (C) current-voltage characteristics as a function of operating voltage for OLED devices having the structure: ITO/(adhesion/injection/molecular component interlayer)/TPD hole transport layer (50 nm)/Alq (60 nm)/Al, where the injection/adhesion component interlayer is prior art Cu(Pc) (10 nm), TAA (15 nm), and TPD-Si$_2$ (40 nm).
Figure 13B:
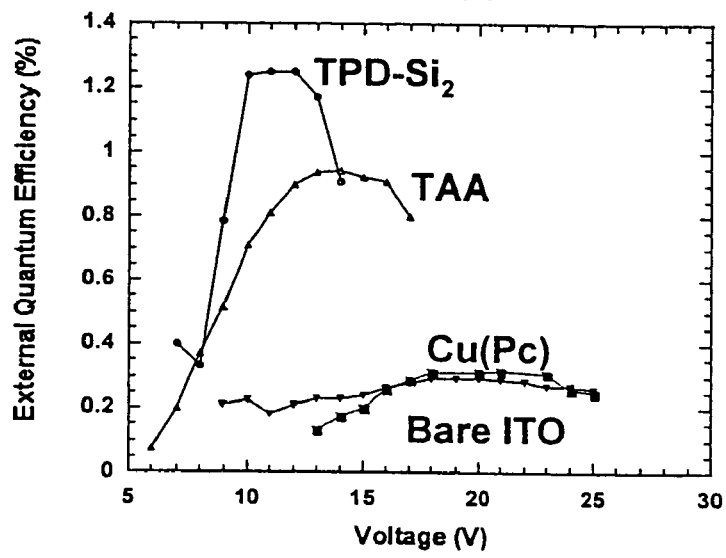
Figure 13C:
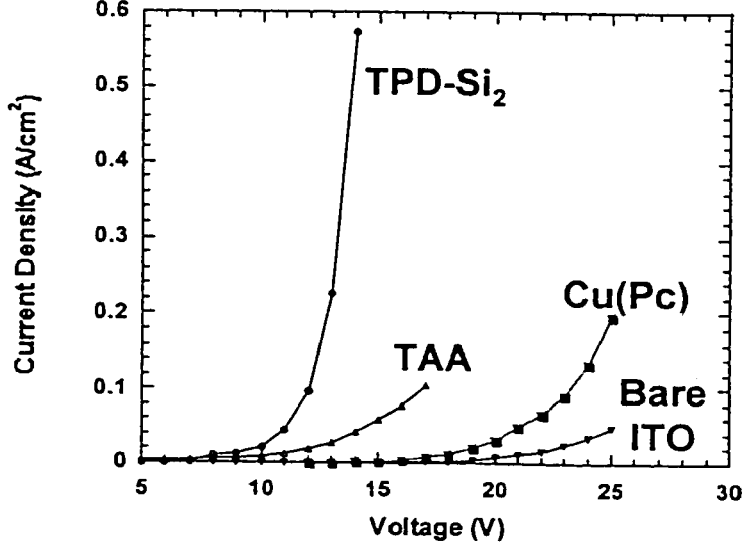

Device characteristics employing spincoated TAA, TPD-Si$_2$, and vapor-deposited Cu(Pc) hole injection layer/adhesion layers in OLEDs having the structure ITO/interlayer/TPD/Alq/Al are compared in FIG. 13. Versus the bare ITO system, all of the molecular/buffer layer-incorporated devices exhibit higher light output, enhanced quantum efficiencies, and lower turn-on voltages. Note that a preferred TPD-Si$_2$ component layer affords ~15,000 cd/m$^2$ of maximum light output, which is 10-100× greater than the bare ITO-based device. Similar increases in ITO/TPD/Alq/Al-type device performance with electrode functionalization have only been reported previously for LiF or CsF-modified Al cathodes, via what remains an unresolved mechanism. It is widely accepted that conventional ITO/TPD/Alq/Al heterostructures are electron-limited due to the low Alq electron mobility and Alq LUMO-Al Fermi level energetic mismatch, thus raising the question of why TPD-Si$_2$ anode modification produces similar effects. It is suggested that under conditions of anode-HTL surface energy mismatch and poor anode-HTL cohesion (an unmodified device of prior art), non-ohmic contacts dominate device behavior, resulting in significant hole injection barriers typical of poor electrode-organic contact.

Example 15

Figure 14:
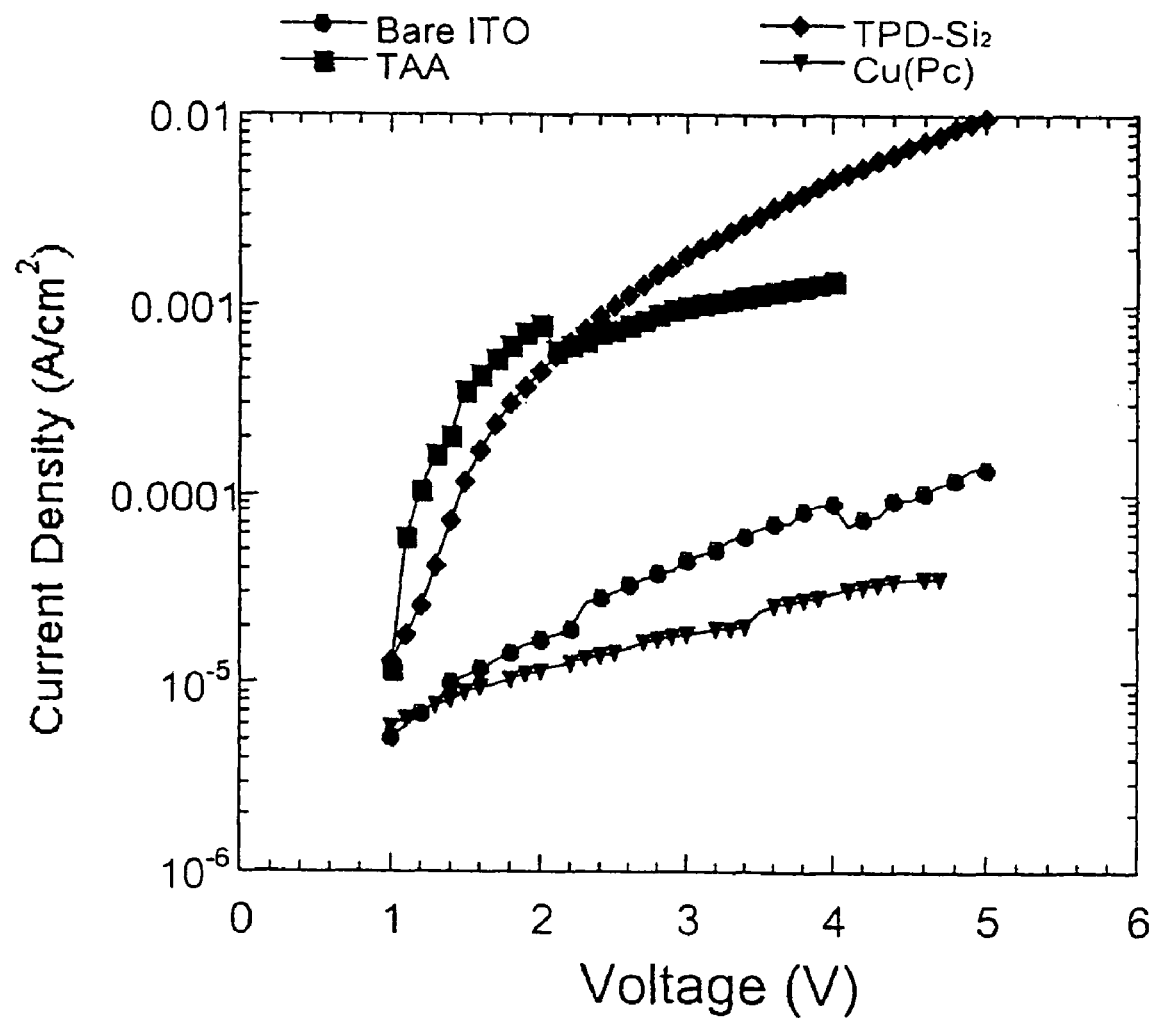
FIG. 14 compares injection characteristics of hole-only devices having the structure ITO/molecular component interlayer/TPD (250 nm)/Au(5 nm)/Al (180 nm) for various anode functionalization layers.

With reference to FIG. 14, TAA and TPD-Si$_2$ interfacial/molecular component layers are significantly more effective injection structures than conventional Cu(Pc) layers. The maximum light output for a Cu(Pc)-based device is ~1500 cd/m$^2$ at 25 V, while that of a TAA-based device is 2600 cd/m$^2$, and at a much lower bias voltage (16 V). The external quantum efficiency of the Cu(Pc)-based device also falls well below those based on TAA and TPD-Si$_2$ anode layers: the maximum quantum efficiency for Cu(Pc) is ~0.3%, in contrast to those of TPD-Si$_2$ (~1.2%) and TAA (~0.9%). The TPD-Si$_2$-functionalized device is most efficient, producing a maximum light output ~10× greater than the Cu(Pc)-buffered device, and ~100× greater than the bare ITO-based device. Improvements observed and differences between TPD-Si$_2$ and silyl-functionalized TAA molecular layers can be explained, without limitation, in relation to: (1) closer aromatic structural similarity of TPD-Si$_2$ to TPD, producing a stronger interlayer affinity and presumably greater π-π interfacial overlap, and (2) the higher triarylamine:siloxane linker ratio in TPD-Si$_2$, consistent with more facile hole hopping via denser triarylamine packing.

Example 16

These findings argue that promotion of ITO-TPD interfacial contact/adhesion leads to more efficient hole injection due to reduced interfacial contact resistance. This hypothesis was tested by examining characteristics of hole-only devices having the structure ITO/molecular interlayer/TPD(250 nm)/Au(6 nm)/Al(80 nm), in which electron injection at the cathode is blocked. Here the Au layer is deposited by rf-sputtering to avoid excessive heating of the TPD underlayer. The hole injection capacity falls in the order TPD-Si$_2$≧TAA>Cu(Pc) >bare ITO (FIG. 14). Compared to bare ITO, the silyl-functionalized TAA- and TPD-Si$_2$-modified anodes enhance the hole current density by 10-100× for the same field strength, with ITO/TPD-Si$_2$ being most effective. Thus, when contact resistance at the OLED anode side is reduced and hole injection increased, the greater electric field induced across the Alq layer enhances electron injection and transport, affording higher light output and comparable or, in the cases where recombination is more probable, enhanced quantum efficiency. In contrast, the present and related data for Cu(Pc) devices show that the Cu(Pc) significantly suppresses hole injection. E. W. Forsythe, M. A. Abkowitz, Y. Gao, *J. Phys. Chem. B* 2000, 104, 3948; S. C. Kim, G. B. Lee, M. Choi, Y. Roh, C. N. Whang, K. Jeong, *Appl. Phys. Lett.* 2001, 78, 1445. It is believed, in light of these results, that Cu(Pc) enhances quantum efficiency via better balancing hole and electron injection fluences, rather than by facilitating hole injection or interfacial stability.

Example 17

Figure 15:
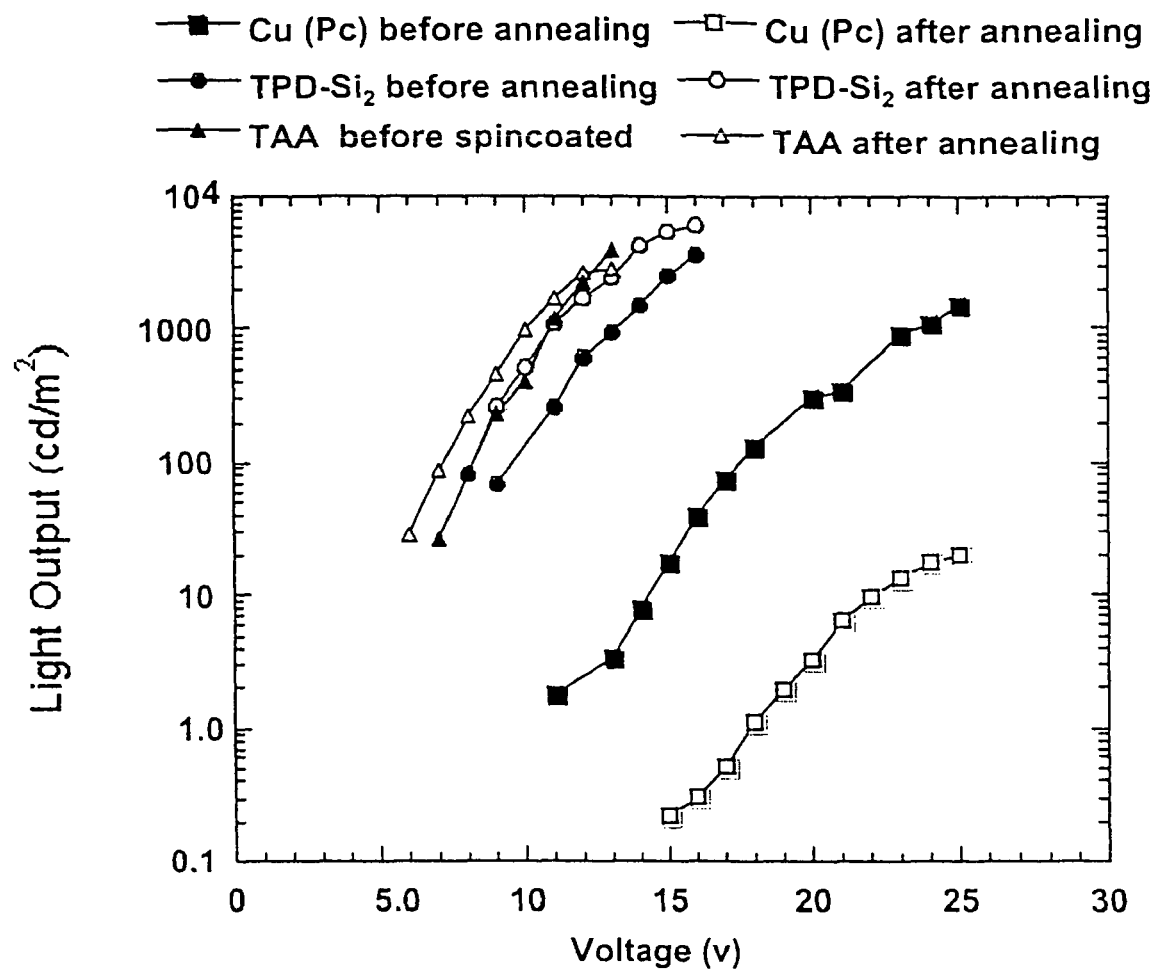
FIG. 15 graphically illustrates by comparison the effect of thermal stressing (90° C. under vacuum) on device characteristics of ITO/(injection/adhesion interlayer)/TPD(50 nm)/Alq(60 nm)/Al (100 nm) devices, where the molecular component interlayer is TPD-Si$_2$ (40 nm), TAA (15 nm), and prior art CuPc (10 nm).

To examine cohesion and crystallization effects on device durability, thermal stress tests were carried out on devices based on bare ITO, having a 10 nm Cu(Pc) interlayer, and having a 40 nm TPD-Si$_2$ interlayer. These were subjected to heating at 95° C. for 0.5 h in vacuum and subsequently examined for changes in luminous response. The irreversible degradation of the bare ITO and Cu(Pc)-based devices upon heating at 95° C. for 0.5 h (FIG. 15) is reasonably ascribed to TPD de-wetting and Cu(Pc)-nucleated TPD crystallization, respectively. Both processes would disrupt the multilayer structure, leading to direct hole injection into, and consequent degradation of, the emissive Alq layer, and possible amplification of pinholes and defects. In contrast, TPD-Si$_2$-buffered molecular layer devices exhibit enhanced performance after heating, which is presumably a consequence of interfacial reconstruction that promotes charge injection. These experiments unambiguously demonstrate that covalently inter-linked alkylsilyl-substituted compounds such as TPD-Si$_2$ and TAA, when used as described herein, offer significant improvements in stabilizing the anode-HTL interface and promoting hole injection.

The results of this and several preceding examples, demonstrate that a spincoated, hole injecting TPD-Si$_2$ layer can significantly increase maximum OLED device luminence (~100×) and quantum efficiency (~6×) by promoting ITO- TPD interfacial cohesion, hence promoting more efficient hole injection. Devices having a TPD-Si$_2$ anode adhesion layer afford a maximum luminance level of 15,000 cd/m$^2$ in absence of dopants or low work function cathodes, while exhibiting excellent thermal stability. In addition, the same results demonstrate that Cu(Pc) interlayers nucleate TPD crystallization upon heating above the T$_g$ of TPD

Example 18

The synthesis of alkylsilyl-functionalized TAA is as was previously described, both herein and in the literature. W. Li, Q. Wang, J. Cui, H. Chou, T. J. Marks, G. E. Jabbour, S. E. Shaheen, B. Kippelen, N. Pegyhambarian, P. Dutta, A. J. Richter, J. Anderson, P. Lee, N. Armstrong, *Adv. Mater.* 1999, 11, 730. TPD, Alq, and Cu(Pc) were obtained from Aldrich and purified by gradient sublimation. All other reagents were used as received unless otherwise indicated. TPD-Si$_2$ can be synthesized as provided elsewhere, herein (see Example 2) or according to FIG. 11B and Examples 19-21, and further characterized by $^1$H NMR spectroscopy and elemental analysis.

Example 19

Figure 11B:
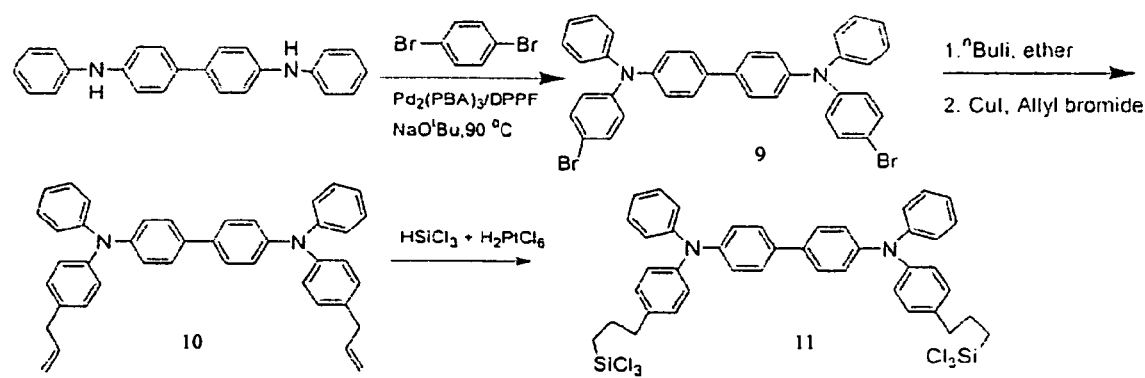
FIG. 11B illustrates one possible scheme for the synthesis of a preferred TPD-$Si_2$ adhesion/injection interlayer molecular precursor. Reference is also made to the procedures described in Example 2.

With reference to FIG. 11B enroute to TPD-Si$_2$, the synthesis of 4,4'-bis[(p-bromophenyl)phenylamino)biphenyl (9). To a solution of tris(dibenzyldeneacetone)dipalladium (0.55 g, 0.6 mmol), and bis-(diphenylphosphino)ferrocene; (0.50 g, 0.9 mmol) in toluene (50 mL), was added 1,4-dibromobenzene (18.9 g, 0.0800 mol) at 25° C., and the solution stirred under N$_2$ for 10 min. Subsequently, sodium tert-butoxide (4.8 g, 0.050 mol) and N,N'-diphenylbenzidine (6.8 g, 0.020 mol) were added, and the reaction mixture stirred at 90° C. for 12 h. The reaction mixture was subsequently cooled to 25° C. and poured into water. The organic layer was separated, and the aqueous layer was extracted with toluene (3×100 mL). The extract was combined with the original organic layer, and the solvent was removed in vacuo to give the crude product. This was purified by chromatography on silica gel using hexane:ethylene chloride (6:1) as the eluant. A white solid (6.9 g) was obtained in 50% yield. $^1$H NMR (CDCl$_3$): δ 6.99 (d, J=8.8 Hz, 4H), 7.02-7.16 (m, 10H), 7.28 (t, J=7.6 Hz, 4H), 7.34 (d, J=8.8 Hz, 4H), 7.45 (d, J=8.4 Hz, 4H).

Example 20

With further reference to FIG. 11B enroute to TPD-Si$_2$, the synthesis of 4,4'-bis[(p-allylphenyl)'phenylamino]biphenyl (10). To a stirring, anhydrous ether solution (10 mL) of 1 (1.02 g, 1.58 mmol) under N$_2$ was added dropwise at 25° C. 1.6 mL (3.5 mmol) n-butyl lithium (2.5 M in hexanes), and the mixture stirred for 2 h. CuI (0.76 g, 4.0 mmol) was then added, the reaction mixture cooled to 0° C., and allyl bromide (0.60 g, 5.0 mmol) added in one portion. The solution was stirred for 14 h, after which time it was quenched with 100 mL saturated aqueous NH$_4$$^+$Cl$^-$ solution, followed by extraction with ether (3×100 mL). The combined ether extracts were washed with water (2×100 mL) and brine (2×100 mL), and dried over anhydrous Na$_2$SO$_4$. Following filtration, solvent was removed in vacuo to yield a yellow oil. Chromatography on silica gel with hexane:ethylene chloride (4:1) afforded 0.63 g white solid. Yield, 70%. $^1$H NMR (CDCl$_3$) δ 3.40 (d, J=10 Hz, 4H), 5.10-5.20 (m, 4H), 6.02 (m, 2H), 6.99-7.10 (m, 2H), 7.10-7.20 (m, 16H), 7.28 (t, J=7.6 Hz, 4H), 7.46 (d, J=8.8 Hz, 4H). Anal. Calcd for C$_{42}$H$_{36}$N$_2$: C, 88.68; H, 6.39; N, 5.23. Found, C, 87.50; H, 6.35; N, 4.93.

Example 21

With reference to FIG. 11B enroute to TPD-Si$_2$, the synthesis of 4,4'-bis[(p-trichlorosilylpropylphenyl)phenylamino]biphenyl (11). To a solution of 2 (0.32 g, 0.55 mol) in 30 mL CH$_2$Cl$_2$ at 25° C. was added a grain of H$_2$PtCl$_6$.xH$_2$O, followed by HSiCl$_3$ (0.73 g, 5.5 mmol). The reaction solution was warmed to 30° C. and stirred for 4 h. Removal of the solvent in vacuum yielded a dark-yellow oil. A mixture of 50 mL pentane and 10 mL toluene was then added. The resulting solid was filtered off, and the filtrate was concentrated under vacuum to a viscous, pale-yellow oil. Yield, 98%. $^1$H NMR (CDCl$_3$): δ1.45 (t, J=7 Hz, 4H), 1.90 (t, J=7 Hz, 4H), 2.70 (brs, 4H), 6.80-7.80 (m, 26H). Anal. Calcd for C$_{42}$H$_{38}$Cl$_6$N$_2$Si$_2$: C, 60.07; H, 4.57. Found, C, 60.52; H, 4.87.

Example 22

With reference to Examples 19-21, a wide variety of arylalkylamine molecular components and their silyl-functionalized analogs can be prepared using straight-forward modifications of the synthetic techniques described herein. For instance, with reference to Example 19, diphenylbenzidene can be mono- or dialkylated with the appropriate haloalkyl reagent to provide the desired arylalkylamine hole transport layer component. As would also be well known to those skilled in the art made aware of this invention, the corresponding silyl-functionalized molecular layer component can be prepared via mono- or dialkylation with the appropriate dihaloalkyl reagent followed by subsequent silation, adopting the procedures illustrated in Examples 20 and 21. Accordingly, by way of further example, the alkylated mono- and diarylamine components, discussed above, and their silyl-functionalized analogs can be prepared to provide the structurally-related molecular and hole transport layers of this invention, and the enhanced performance and/or hole injection resulting therefrom.

Example 23

TPD-Si$_2$ and TAA Thin Film Deposition and Characterization. Indium tin oxide (ITO) glass sheets with a resistance of 20Ω/□ from Donnelly Corp. were subjected to a standard literature cleaning procedure. TAA and TPD-Si$_2$-based buffer layers were spincoated onto cleaned ITO surfaces from their respective toluene solutions (10 mg/mL) at 2 Krpm, followed by curing in moist air at 110° C. for 15 min. Cyclic voltammetry of spincoated TPD-Si$_2$ films on ITO was performed with a BAS 100 electrochemical workstation (scan rate, 100 mV/s; Ag wire pseudo-reference electrode, Pt wire counter electrode, supporting electrolyte, 0.1 M TBAHFP in anhydrous MeCN). For TPD-Si$_2$ film contiguity assessment, 1.0 mM ferrocene in 0.1 M TBAHFP/MeCN was used as the probe. Thermogravimetric analysis (TGA) was carried out on an SDT 2960 DTA-TGA instrument with a scan rate of 10° C./min under N$_2$. TGA sample preparation involved drop-coating a TPD-Si$_2$ solution in toluene (10 mM) onto clean glass substrates under ambient conditions. Following solvent evaporation, the TPD-Si$_2$-coated slides were cured at 120° C. for 1 h. Upon cooling, the films were detached from the glass substrates using a razor blade and collected as powders for TGA characterization.

Example 24

ITO/Buffer Layer/TPD Interfacial Stability Studies. TPD de-cohesion analysis of the interfacial structures ITO/buffer layer/TPD (100 nm) (spincoated TPD-Si$_2$, spincoated TAA, vapor-deposited Cu(Pc)) were carried out in the following manner. Following vapor deposition of 50-100 nm TPD films onto the respective buffer layer-coated ITO substrates, the samples were annealed at 80-100° C. under N$_2$ for 1.0 h, and the film morphology subsequently imaged by optical microscopy and AFM.

Example 25

OLED Device Fabrication. OLED devices of the structure: ITO/interlayer/TPD(50 nm)/Alq(60 nm)/Al(100 nm) were fabricated using standard vacuum deposition procedures (twin evaporators interfaced to a <1 ppm O$_2$ glove box facility). Deposition rates for organic and metal were 2-4 Å/sec and 1-2 Å/sec respectively, at 1×10$^{-6}$ Torr. The OLED devices were characterized inside a sealed aluminum sample container under N$_2$ using instrumentation described elsewhere. J. Cui, Q. Huang, Q. Wang, T. J. Marks, *Langmuir* 2001, 17, 2051; W. Li, Q. Wang, J. Cui, H. Chou, T. J. Marks, G. E. Jabbour, S. E. Shaheen, B. Kippelen, N. Pegyhambarian, P. Dutta, A. J. Richter, J. Anderson, P. Lee, N. Armstrong, *Adv. Mater.* 1999, 11, 730.

Example 26

Device Thermal Stability Evaluations. OLED devices were subjected to heating under vacuum at 95° C. for 0.5 h, and were subsequently evaluated for I-V and L-V characteristics as described above.

Example 27

Materials and Methods Relating Examples 28-38. All manipulations of air/moisture-sensitive materials were carried out on a dual-manifold Schlenk line or in a nitrogen-filled glovebox. Ether and methylene chloride were distilled before use from sodium/benzophenone ketyl or calcium hydride, respectively. Toluene was dried using activated alumina and Q5 columns and tested by benzyphenone ketyl in ether solution. All reagents were used as received unless otherwise indicated. NMR spectra were obtained on Varian VXR-400 or 500 MHz NMR instruments. MS analyses were conducted on a Micromass Quattro II Triple Quadrupole HPLC/MS/MS mass spectrometer. Elemental analyses were carried out by Midwest Microlabs. UV-visible absorption spectra of SAM-coated quartz plates were obtained on a Cary 1E UV-vis spectrometer. Cyclic voltammetry was performed with a BAS 100 electrochemical workstation (SAM-coated ITO with ~1 cm$^2$ area working electrodes, Ag wire pseudo-reference electrode, Pt wire counter electrode, supporting electrolyte, 0.1 M TBAHFP in anhydrous MeCN). TBAHFP was recrystallized from an ethylacetate/hexanes solution and dried in vacuo at 100° C. for 10 h. AFM images were obtained on a Nanoscope III AFM in the contact mode. Specular x-ray reflectivity experiments on coated single-crystal Si (111) substrates were performed on the Naval Research Laboratory X23B beamline at the National Synchrotron Light Source. Advancing aqueous angles were measured on SAM-coated ITO substrates immediately after the self-assembly process.

Example 28

Figure 11C:
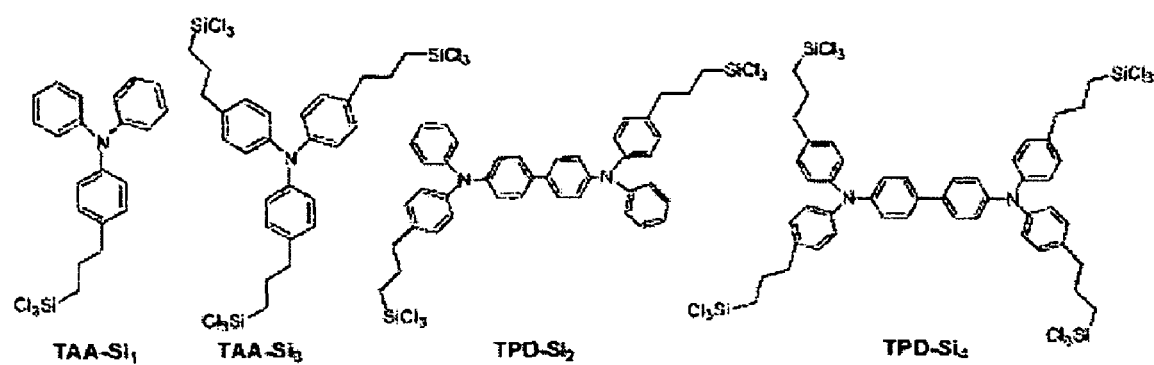
FIG. 11C provides structural formulae, with designations described elsewhere herein, in accordance with the compounds of FIGS. 2A, 2C-E. Reference is made to the synthetic procedures of Examples 27-28 and the comparative studies of Examples 29-38.

With reference to the compounds of FIG. 11C and the schematic of FIG. 11D, compounds 12-18 were prepared as follows:

Example 28a

Synthesis of 4,4'-bis[(p-bromophenyl)phenylamino)]biphenyl (12). To a solution of tris(dibenzyldeneacetone)dipalladium (0.55 g, 0.60 mmol) and bis-(diphenylphosphino)ferrocene (0.50 g, 0.90 mmol) in 50 mL toluene, was added 1,4-dibromobenzene (18.9 g, 0.0800 mol) at 25° C., and the solution stirred under N$_2$ for 10 min. Subsequently, sodium tert-butoxide (4.8 g, 0.050 mol) and N,N'-diphenylbenzidine (6.8 g, 0.020 mol) were added, and the reaction mixture stirred at 90° C. for 12 h. The reaction mixture was subsequently cooled to 25° C. and poured into water. The organic layer was separated, and the aqueous layer was extracted with toluene (3×100 mL). The extract was combined with the original organic layer, and the solvent was removed under vacuum to give the resultant crude product. The crude product was purified by chromatography on silica gel using hexane:ethylene chloride (6:1) as the eluant. Compound 12 was obtained as a white solid (6.9 g) in 50% yield. $^1$H NMR (CDCl$_3$): δ 6.99 (d, J=8.8 Hz, 4H), 7.02-7.16 (m, 10H), 7.28 (t, J=7.6 Hz, 4H), 7.34 (d, J=8.8 Hz, 4H), 7.45 (d, J=8.4 Hz, 4H).

Example 28b

Synthesis of N,N,N',N'-tetrakis-(p-bromophenyl)-biphenyl-4,4'-diamine (13). To a stirring chloroform solution (20 mL) of 12 (0.5 g, 0.77 mmol), tetrabutylammonium tribromide (0.74 g, 1.54 mmol) was added in one portion at 25° C. The reaction was monitored by TLC (elution hexane:ether=7:1) and was found to be complete after 0.5 h. The reaction mixture was then washed with aqueous sodium thiosulfate and water until pH=7, followed by removing solvent under vacuum to afford a yellowish solid. Next, 500 mL ether was added and the solution was washed with water (3×100 mL) and brine (2×100 mL), and dried over anhydrous Na$_2$SO$_4$. Following filtration, solvent was removed in vacuum to yield a white solid Recrystallization from chloroform:hexane (1:10) afforded 0.49 g of 13 as a white solid. Yield, 79%. $_1$H NMR (CDCl$_3$): δ 6.99 (d, J=9 Hz, 8H), 7.11 (d, J=9 Hz 4H), 7.38 (d, J=9 Hz, 8H), 7.47 (d, J=9 Hz, 4H), MS (m/z): 804.8 [M, 100]

Example 28c

Synthesis of N,N,N',N'-tetrakis-(p-allylphenyl)-biphenyl-4,4'-diamine (14). To a stirring, anhydrous ether solution (8 mL) of 13 (0.050 g, 0.062 mmol) under inert atmosphere, was added dropwise at 25° C. n-butyl lithium (1.6 M in hexanes, 0.31 mL, 0.50 mmol), and the mixture stirred for 2 h. The reaction mixture was then cooled to 0° C. followed by addition of copper iodide(I) (0.1 g, 0.5 mmol). After stirring for 5 min., allyl bromide (0.07 g, 0.6 mmol) was added in one portion. The solution was warmed up to 25° C. gradually and stirred for 12 h, after which time it was quenched with 100 mL saturated aqueous NH$_4^+$Cl$^-$ solution, followed by extraction with ether (3×100 mL). The combined ether extracts were washed with water (2×100 mL) and brine (2×100 mL), and dried over anhydrous Na$_2$SO$_4$. Following filtration, solvent was removed in vacuum to yield an oil. Chromatography on silica gel with hexane:methylene chloride (10:1) afforded 0.027 g of 14 as a white solid. Yield, 68%. $^1$H NMR (CDCl$_3$): δ 3.37 (brs, J=10 Hz, 8H), 5.06-5.12 (m, 8H), 5.95-6.03 (m, 4H), 7.08 (brs, 20H), 7.41 (brs, 4H). Anal. Calcd for $C_{48}H_{44}N_2$: C, 88.83; H, 6.85; N, 4.32. Found, C, 88.89; H, 6.91; N, 4.28.

Example 28d

Synthesis of N,N,N',N'-tetrakis[(p-trichlorosilylpropyl)-phenyl]-biphenyl-4,4'-diamine (15). To a solution of 3 (0.040 g, 0.062 mmol) in 25 mL dry $CH_2Cl_2$ at 25° C. under inert atmosphere was added $H_2PtCl_6 \cdot xH_2O$ (0.001 g), followed by trichlorosilane (0.042 g, 0.31 mmol). The reaction solution was warmed to 30° C. and monitored by NMR until the completion of reaction after 6 h. Removal of the solvent in vacuum yielded an oil. Next, 20 mL dry toluene was added to the residue and the resulting solution filtered into a Schlenk flask by cannula. The filtrate was concentrated under vacuum to give 15 as a pale-yellow oil. Yield, 98%. $^1$H NMR (benzene-$d_6$): δ0.91 (brs, 4H), 1.56 (brs, 8H), 2.21 (brs, 8H), 6.81-7.39 (m, 24H).

Example 28e

Synthesis of 4-bromo-phenyl-diphenyl-amine (16). To a solution of tris(dibenzylideneacetone)dipalladium (0.41 g, 0.44 mmol), and bis-(diphenylphosphino)ferrocene (0.37 g, 0.67 mmol) in 50 mL dry toluene under inert atmosphere, was added sodium tert-butoxide (4.2 g, 0.04 mol) at 25° C. The mixture was stirred for 15 min followed by addition of 1,4-dibromobenzene (27.9 g, 0.12 mol), and stirred for another 15 min. Diphenylamine (5.0 g, 0.029 mmol) were added, and the reaction mixture was heated to 90° C. for 15 h. The reaction mixture was subsequently cooled to 25° C. and poured into water. The organic layer was separated, and the aqueous layer was extracted with toluene (3×100 mL). The extracts were combined with the original organic layer, and the solvent was removed under vacuum to give the resultant crude product. The crude product was purified by chromatography on silica gel using hexane:ethylene chloride (6:1) as the eluant. Compound 16 was obtained as a white solid (5.6 g) in 59% yield. $^1$H NMR (CDCl$_3$): δ 6.94 (d, J=8 Hz, 2H), 7.01-7.08 (m, 6H), 7.23-7.27 (m, 4H), 7.32 (d, J=8 Hz, 2H). MS (m/z): 323.2 [M, 100].

Example 28f

Synthesis of 4-allyl-phenyl-diphenyl-amine (17). To a stirring, anhydrous ether solution (20 mL) of 16 (0.58 g, 1.8 mmol) under inert atmosphere, n-butyl lithium (1.6 M in hexanes, 1.2 mL, 1.92 mmol) was added slowly at −50° C., and the mixture was stirred at −50° C. for 15 min, and gradually warmed up to 25° C. After 3 h, copper iodide(I) (0.51 g, 2.7 mmol) was added followed by dropwise addition of allyl bromide (0.32 g, 2.7 mmol). The solution was stirred for 12 h, followed by quenching with 100 mL saturated aqueous NH$_4^+$ Cl$^-$ solution and extraction with ether (3×100 mL). The combined ether extracts were washed with water (2×100 mL) and brine (2×100 mL), and dried over anhydrous Na$_2$SO$_4$. Following filtration, solvent was removed in vacuum to yield an oil. Chromatography on silica gel with hexane:methylene chloride (4:1) afforded 0.18 g of 17 as a colorless-oil. Yield, 35%. $^1$H NMR (CDCl$_3$): δ 3.40 (d, J=7.5 Hz, 2H), 5.11-5.32 (m, 2H), 5.98-6.07 (m, 1H), 6.98-7.15 (m, 8H), 7.22-7.37 (m, 6H). Anal. Calcd for $C_{21}H_{19}N$: C, 88.36; H, 6.72; N, 4.91. Found, C, 88.34; H, 6.10; N, 4.24.

Example 28g

Synthesis of Diphenyl-[4-(3-trichlorosilyl-propyl)-phenyl]-amine (18). To a solution of 17 (0.18 g, 0.65 mmol) in 25 mL dry $CH_2Cl_2$ at 25° C. under inert atmosphere was added $H_2PtCl_6 \cdot xH_2O$ (0.001 g), followed by trichlorosilane (0.88 g, 6.5 mmol). The reaction solution was warmed to 30° C. and monitored by NMR until the completion of reaction after 4 h. Removal of the solvent in vacuum yielded a oil. 20 mL dry toluene was added to the residue and filtered into a Schlenk flask by cannula. The filtrate was concentrated under vacuum to give 18 as a oil. Yield, 98%. $^1$H NMR (benzene): δ0.90 (t, J=8 Hz, 2H), 1.55 (m, 2H), 2.20 (t, J=8 Hz, 2H), 6.75-6.83 (m, 4H), 6.98-7.14 (m, 10H).

Example 29

A series of alkyltrichlorosilyl compounds was synthesized and purified, as described above (see, more particularly, FIG. 11D). Self-limited anaerobic chemisorption of these compounds onto smooth (~2.5 nm RMS roughness), plasma-cleaned ITO surfaces was carried out by immersing ITO substrates in 1.0 mM toluene solutions, followed by rinsing, drying and curing. Adsorbate characterization included AFM, aqueous contact angles, optica spectroscopy, cyclic voltammetry, XPS, UPS, and X-ray reflectivity (XRR), revealing formation of conformal, largely pinhole-free self assembled monolayers (SAMs) with sub-nanometer thickness control and essentially identical aggregate surface energies, ionization potentials, and coverages (Table 1, below). Protocols for OLED fabrication and data acquisition are provided in examples 33-38.

The effect of SAM structure on ITO-organic interfacial hole injection was first investigated by fabricating hole-only devices (having structures ITO/SAM/N,N-naphathyl-N,'N-phenyl-biphenyl-4,4'-di-amine (NPB, 400 nm)/Au/Al). Since the only difference in the four types of devices is SAM molecular structure, the results clearly reveal a significant structure sensitivity of hole injection across the nano interfacial region. With reference to the data obtained for the hole-only devices described in several preceding example(s), hole current densities at 25 V are ~0.0004 A/cm$^2$ (TAA-Si$_3$) <~0.004 A/cm$^2$ (TAA-Si$_1$)<~0.01 A/cm$^2$ (TPD-Si$_2$)<~0.04 A/cm$^2$ (TPD-Si$_4$); hole injection fluences vary by 1 to 2 orders of magnitude. The current densities are somewhat lower than those in OLEDs studied below, principally due to the thicker HTL (hole transport layer) deposited in the hole-only devices.

Example 30

OLEDs (having structures ITO/(SAM)/NPB/tris-(8-hydroxyquinolato)aluminum (AlQ): 1% diisoamylquinacridone (DlQA)/Al) were next fabricated to examine SAM structure effects on EL response, which are also significant. Bare ITO and phenylsilane SAM-coated ITO-based devices were also fabricated for comparison. In Al cathode OLEDs, luminances at 20 mA/cm$^2$ (a standard current density for device evaluation) are 200 cd/m$^2$ (TPD-Si$_4$)<230 cd/m$^2$ (TPD-Si$_2$)<400 cd/m$^2$ (TAA-Si$_1$)<570 cd/m$^2$ (TAA-Si$_3$). This order of current efficiency is opposite to that of the hole current densities measured above and can be understood in terms of electron injection-limited electron-hole recombination events. Appreciable forward external quantum efficiency ($\eta_{ext}$) variations possibly evidence large, anode-organic interface effects on OLED charge recombination. Compared to bare ITO-based devices, SAM-induced OLED performance enhancement is observed, with the modest phenylsilane SAM improvement mainly attributable to improved ITO anode-HTL contact via surface energy matching. Comparison between phenyl and triarylamine silane SAMs indicates that the latter result in lower anode-HTL hole injection barriers, agreeing with lower turn-on and operating voltages at identical luminance.

Example 31

In a second device configuration with enhanced electron injection and a hole-blocking layer (ITO/(SAM)/NPB/AlQ:1% DIQA/2,9-dimethyl-4,7-diphenyl-1,10-phenanthroline (BCP)/Li/AgMg), the hole-electron density imbalance is substantially alleviated, and more efficient recombination is expected. This is indeed observed, with the maximum luminance and $\eta_{ext}$ achieved by TPD-Si$_4$-based OLEDs (~70 000 cd/M$^2$ and 2.1%, respectively) nearly 1 order of magnitude and 5 times greater, respectively, than the comparable device structure of example 30. Strong SAM structure-OLED response correlations are again observed, compared to a phenylsilane based device, with the quantum efficiency ordering reflecting better recombination balance for the superior hole injection SAMs. The light output of the TPD-Si$_4$-based OLED is ~1.5 to 3 times brighter than that of TPD-Si$_2$ (~50 000 cd/m$^2$), TAA-Si$_1$ (~45 000 cd/m$^2$), and TAA-Si$_3$ (~23 000 cd/m$^2$) at identical bias.

Example 32

Cyclic voltammetry of the SAMs on ITO (TBAHFP/CH$_3$CN) reveals $E_{ox}/E_{red}$ peak separations increasing in the order 331 mV (TPD-Si$_4$)<345 mV (TPD-Si$_2$)<382 mV (TAA-Si$_1$)<466 mV (TAA-Si$_3$). Such data can be used to estimate interfacial electron-transfer rates for strongly absorbed redox-active sites and also reflect absorbate structural inhomogeneity, interactions, and electrode-redox center spacings. All other factors being equal, larger peak separations qualitatively correlate with slower interfacial electron transfer. Interestingly, this electrochemical index of heterogeneous charge injection and transport efficiency correlates closely with the solid-state hole-only device of example 29, with respect to injection and transport capacity: TPD-Si$_4$>TPD-Si$_2$>TAA-Si$_1$>TAA-Si$_3$. Without limitation to any one theory or mode of operation, the structural basis for these variations may be associated with different SAM reorganization energies and different triarylamine cores having different E° values. Additionally, the distance from the triarylamine cores to the ITO surface varies as a function of molecule geometry and linker density. TAA-Si$_3$ and TPD-Si$_4$ have three or four silyl linkers, respectively, while TAA-Si$_1$ and TPD-Si$_2$ have one or two, respectively. The former two compounds may predominantly lie flat on the ITO surface, minimizing the triarylamine-anode distance, while the latter two components may "stand up," leading to different charge injection and transport characteristics. The XRR-derived SAM thickness and roughness data, combined with molecular modeling, show that TAA-Si$_3$ in fact anchors largely via one linker rather than three, similar to situations seen previously, while TPD-Si$_4$ adopts both "flat" and "upright" orientations, yielding a rough surface. This can be correlated with the greater charge transport capacity due to the smaller NAr$_3$-ITO anode spacing. Finally, differing intermolecular interactions between triarylamine cores likely arise from the differing molecular shapes and linker densities and should also affect interfacial charge injection and transport.

TABLE 1

Characteristics of Anode Functionalization Layers[a]

|  | TAA-Si$_1$ | TAA-Si$_3$ | TPD-Si$_2$ | TPD-Si$_4$ |
|---|---|---|---|---|
| $\lambda_{max}$ (nm) | 303 | 304 | 352 | 352 |
| thickness (nm)[b] | 1.2 | 1.4 | 1.8 | 1.6[c] |
| RMS roughness (nm)[b] | 0.4 | 0.7 | 0.7 | 1.3 |
| aq contact angle (deg) | 90 | 87 | 90 | 90 |
| $E_{p,a}/E_{p,c}$ (V)[d] | 1.180/0.798 | 1.200/0.734 | 1.160/0.815 | 1.130/0.799 |
| coverage Γ ($\times 10^{-10}$ mol/cm$^2$)[d] | 4.5 | 4.2 | 2.5[f] | 2.1[f] |
| $\Delta E_{p,1/2}$ (mV)[g] | 340 | 460 | 350 | 440 |
| JP (eV)[h] |  |  | 5.8 | 6.1 |

[a]Experimental details in Supporting Information.
[b]From X-ray reflectivity of samples identically deposited on oxide-coated (111)Si.
[c]This parameter is uncertain due to surface roughness.
[d]From cyclic voltammetry (10 V/s).
[e]Estimated by CV (0.1 V/s).
[f]CV coverage consistent with XRR data assuming two-electron process.
[g]0.1 V/s scan rate. $\Delta E_{p,1/2}$ > 90.6/n mV, indicating redox site interactions, site heterogeneity, or both.
[h]From UPS.

Example 33

General self-assembly procedure on ITO, quartz or Si wafer substrates. Taking TAA-Si$_1$ as an example, pre-cleaned ITO substrates were immersed in dry toluene (50 mL) to which 0.5 mL of compound 18 in dry toluene solution (0.1 M) was added. After heating at ~80° C. for 1 h, the toluene solution was removed by cannula and substrates were rinsed with dry toluene (2×50 mL) and wet acetone. Baking the substrates at 110° C./100 mmHg in a vacuum oven for 1 h completed the self-assembly process.

Example 34

SAM characterization:cyclic voltammetry. SAM-coated ITO, silver wire and Pt wire were used as the working electrode, reference electrode, and counter electrode, respectively. All experiments were carried out in 0.1 M acetonitrile solution of tetrabutylammonium hexafluorophosphate as the electrolyte at scan rate 0.1 V/s, or 10 V/s, respectively.

Example 35

SAM (on Si substrates) characterization: X-ray reflectivity.

TABLE 2

|  | TPD-Si$_2$ | TPD-Si$_4$ | TAA-Si$_3$ | TAA-Si$_1$ |
|---|---|---|---|---|
| Electron density (eÅ$^{-3}$) | 0.32-0.35 | 0.30-0.33 | 0.32-0.34 | 0.31 |
| Roughness (Å) | 7.4-8.2 | 12-14 | 7.5 | 3.9-4.0 |
| Thickness (Å) | 17.7-17.9 | 16.3 | 13.6 | 11.0-11.1 |
| Footprint (Å$^2$) | 51-58 | 80-98 | 51-66 | 44-50 |
| Calculated Coverage Γ ($\times 10^{-10}$ mol/cm$^2$)* | 2.8-3.3 | 1.7-2.1 | 2.5-3.0 | 3.3-3.8 |

*Based on electron density profiles obtained from X-ray reflectivity measurements, the number of electrons per unit of substrate area for SAMs are calculated as $N_{SAM} = \int \rho(z)dz$. The molecular footprints were calculated as $N_{mol}/N_{SAM}$, where $N_{mol}$ is the calculated number of electrons in one molecular unit.

Example 36

SAM characterization: pinhole study by cyclic voltammetry. SAM-coated ITO, silver wire and Pt wire were used as the working electrode, reference electrode, and counter electrode, respectively. All experiments were carried out in 0.1 M acetonitrile solution of tetrabutylammonium hexafluorophosphate as the electrolyte and 0.001 M ferrocene as the internal pin hole probe. Scan rate 0.1 V/s.

Example 37

SAM-coated ITO-based OLED fabrication. The SAM coated substrates were transferred to a glove box/twin evaporator fabrication facilities, followed by thermal evaporation at $1 \times 10^{-7}$ Torr of NPB (20 nm), AlQ/1% DIQA (50 nm), BCP (20 nm), aluminum (140 nm), lithium (1 nm), and Mg/Ag (1:9, 100 nm), corresponding to the desired OLED structures. NPB, AlQ, DIQA, and BCP were purified by gradient vacuum sublimation before use. The 0.2×0.5 cm² OLED emitting areas were defined by shadow masks. Light output and J-V characteristics were measured with a Keithley 2400 source meter and an IL 1700 research radiometer at 25° C. under ambient atmosphere. External quantum efficiencies and power efficiencies were estimated from current density vs. voltage and luminance vs. current density characteristics.

Example 38

SAM-coated ITO-based hole-only device fabrication. NPB (400 nm), Au (6 nm), and Al (100 nm) were evaporated onto the SAM coated ITO substrates. They were characterized with the same procedure as described above.

The preceding examples present evidence for significant OLED anode-organic interfacial molecular structure effects on hole injection and/or transfer and EL properties, and show that these correlate with heterogeneous electron-transfer characteristics. Chemically tuning the interface structure represents an effective approach to studying nanoscale injection layers and yields OLEDs with high brightness (~70 000 cd/m²), low turn-on voltages (~4 V), and high current efficiencies (~8 cd/A).

Example 39

Figure 11D:
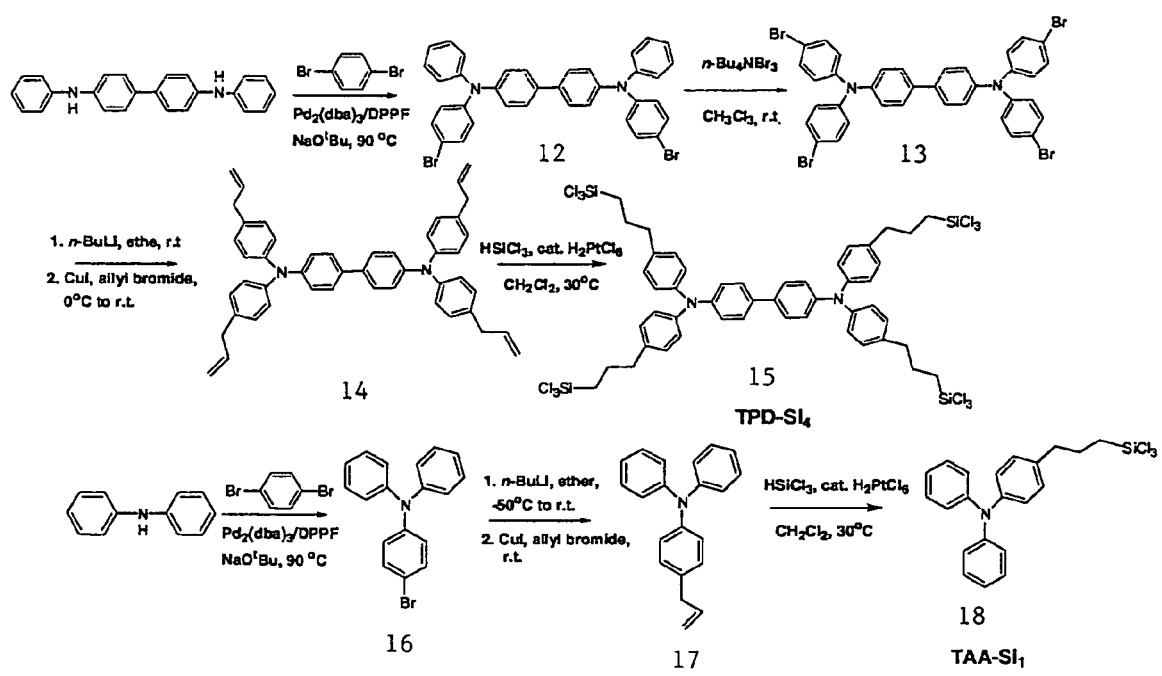
FIG. 11D illustrates schemes for the synthesis of two compounds of FIG. 11C, such schemes analogous to the syntheses described elsewhere herein, in particular in Example 2 and FIGS. 2G and 11B.

With reference to examples 2-3, 28a-g and FIGS. 2G, 11B and 11D, and the synthetic techniques described elsewhere herein, various other hole transport compounds of FIGS. 2A, 2C and 2D-F can be prepared using—in any possible combination—the starting materials and reagents of Table 3, where notes a-e reference commercial source or literature preparation. It will be understood in the art that various other commercially- or synthetically-available aromatic amines and halides and alkene halides can be used as described herein or with straight-forward modification of such techniques, without undue experimentation. Likewise, other available silane reagents can be employed to provide hydrolyzable silyl groups and the corresponding silyl-functionalized hole transport compounds, in accordance with this invention.

TABLE 3

Reagents for Preparation of Silyl-Functionalized Aromatic Amine Hole Transport Compounds

| Aromatic Amine | Aromatic Halide | Alkene Halide | Silane |
| --- | --- | --- | --- |
| 2-Naphthalenamine[a] | 1-Bromo-napthlene[a] | Allylbromide[a] | Trimethoxysilane[a] |
| Biphenyl amine[a] | 1,8-Dibromo-anthracene[b] | 5-Bromo-pentene[a] | Chlorodimethoxysilane |
| N,N'-diphenylbenzidine[a] | 1-Bromo-anthracene[d] | Vinylbromide[a] | Dichloroethoxysilane |
| N-Phenyl-2-naphthylamine[a] | 1,8-Dibromo-anthracene[b] | 4-Bromobutene[a] | Trichlorosilane[a] |
| N-2-Naphthyl-1-naphthylamine[e] | Biphenyl bromide[a] | allylbromide[a] | Triethoxysilane[a] |

[a]Aldrich
[b]Haenel, M. W.; Jakubik, D.; Krueger, C.; Betz, P. Chem. Ber. 1991, 124, 333-336.
[c]Gelest
[d]Netka, J.; Crump, S. L.; Rickborn, B.J. Org. Chem. 1986, 51, 1189-1199.
[e]ASDI Product List While the principles of this invention have been described in connection with specific embodiments, it should be understood clearly that these descriptions are added only by way of example and are not intended to limit, in any way, the scope of this invention. For instance, the present invention can be applied more specifically to the construction of second-order nonlinear optical materials as have been described in U.S. Pat. No. 5,156,918 which is incorporated herein by reference in its entirety. Likewise, the present invention can be used in conjunction with the preparation of optical waveguides. Another advantages and features will become apparent from the claims hereinafter, with the scope of the claims determined by the reasonable equivalents, as understood by those skilled in the art.

We claim:

1. A hole transport compound having a formula

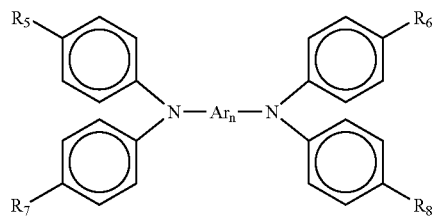

wherein Ar is arylene; n is an integer from 1-4 and $R_5$-$R_8$ are independently selected from H and a moiety comprising a hydrolyzable silane, wherein the hydrolyzable silane comprises three hydrolyzable groups, and wherein at least two of $R_5$-$R_8$ are a moiety comprising the hydrolyzable silane.

2. The hole transport compound of claim 1 wherein Ar is phenylene and n is 2.

3. The hole transport compound according to claim 1 wherein each moiety comprising the hydrolyzable silane is a hydrolyzable silane alkyl group.

4. The hole transport compound according to claim 3 wherein the silyl portion of each silane alkyl group is selected from a trihalogenated silane and a trialkoxylated silane.

5. The hole transport compound according to claim 4 wherein $R_5$ and $R_6$ are hydrogen and $R_7$ and $R_8$ are selected from trihalogenated silane alkyl and trialkoxylated silane alkyl.

6. A hole transport compound having a formula

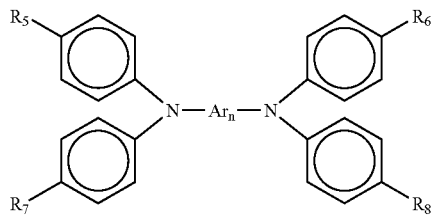

wherein Ar is arylene; n is an integer from 1-4 and $R_5$-$R_8$ are independently selected from H and a moiety comprising a hydrolyzable silane, wherein the hydrolyzable silane comprises three hydrolyzable groups, and wherein at least one of $R_5$-$R_8$ is the moiety comprising the hydrolyzable silane, wherein the hydrolyzable silane is a hydrolyzable silane alkyl group.

7. The hole transport compound of claim 6 wherein Ar is phenylene and n is 2.

8. The hole transport compound according to claim 6 wherein the silyl portion of each silane alkyl group is selected from a trihalogenated silane and a trialkoxylated silane.

* * * * *